(12) United States Patent
Chang et al.

(10) Patent No.: US 9,782,248 B2
(45) Date of Patent: Oct. 10, 2017

(54) DECELLULARIZED COMPOSITE TISSUE BIOSCAFFOLDS FOR MUSCULOSKELETAL TISSUE INTERFACE RECONSTRUCTION AND METHODS OF PRODUCTION

(71) Applicant: The Board of Trustees of the Leland Stanford Junior University, Palo Alto, CA (US)

(72) Inventors: James Chang, Stanford, CA (US); Colin Woon, Chicago, IL (US); Hung Pham, Milpitas, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 551 days.

(21) Appl. No.: 14/363,283

(22) PCT Filed: Dec. 7, 2012

(86) PCT No.: PCT/US2012/068555
§ 371 (c)(1),
(2) Date: Jun. 5, 2014

(87) PCT Pub. No.: WO2013/086404
PCT Pub. Date: Jun. 13, 2013

(65) Prior Publication Data
US 2014/0350677 A1    Nov. 27, 2014

Related U.S. Application Data

(60) Provisional application No. 61/568,938, filed on Dec. 9, 2011.

(51) Int. Cl.
*A61F 2/08*   (2006.01)
*A61L 27/36*  (2006.01)
*A61K 35/32*  (2015.01)

(52) U.S. Cl.
CPC ............... *A61F 2/08* (2013.01); *A61K 35/32* (2013.01); *A61L 27/3683* (2013.01); *A61L 27/3687* (2013.01); *A61L 27/3691* (2013.01)

(58) Field of Classification Search
CPC ..... A61F 2/08; A61L 27/3683; A61L 27/3687
See application file for complete search history.

(56) References Cited

U.S. PATENT DOCUMENTS

| | | | |
|---|---|---|---|
| 2005/0229323 A1* | 10/2005 | Mills | A61L 27/50 8/94.11 |
| 2007/0248638 A1 | 10/2007 | Van Dyke et al. | |

(Continued)

*Primary Examiner* — Jason-Dennis Stewart
(74) *Attorney, Agent, or Firm* — Stanford University; Andrea Blecken

(57) ABSTRACT

One aspect of the present invention is a method of producing a decellularized composite tissue bioscaffold for musculoskeletal tissue interface reconstruction by physicochemically treating a musculoskeletal tissue interface isolated from allogeneic sources. In certain embodiments, such musculoskeletal tissue interfaces can also be isolated from xenogeneic sources. The method comprises treatment of the interface with detergents, chemical oxidants and ultrasonic energy, and wash steps in between to remove residual detergents as well as oxidants. The resulting bioscaffold may be freeze-dried or lyophilized, sterilized and aseptically packaged for subsequent use.

15 Claims, 16 Drawing Sheets

(56) References Cited

U.S. PATENT DOCUMENTS

| | | |
|---|---|---|
| 2007/0260109 A1 | 11/2007 | Squillace et al. |
| 2009/0124552 A1 | 5/2009 | Hill et al. |
| 2009/0325295 A1 | 12/2009 | Masini et al. |
| 2010/0266559 A1 | 10/2010 | Nataraj et al. |

* cited by examiner

DECELLULARIZED COMPOSITE TISSUE BIOSCAFFOLDS FOR MUSCULOSKELETAL TISSUE INTERFACE RECONSTRUCTION AND METHODS OF PRODUCTION

RELATED APPLICATION

This application claims priority and other benefits from U.S. Provisional Patent Application Ser. No. 61/568,938, filed Dec. 9, 2012, entitled "Decellularized composite tissue bioscaffolds and methods of production". Its entire content is specifically incorporated herein by reference. Furthermore, this application claims priority as the U.S. national stage application of PCT/US12/68555, having an international filing date of Dec. 7, 2012, which is hereby incorporated in its entirety.

TECHNICAL FIELD OF THE INVENTION

The present invention relates to the field of tissue engineering bioscaffolds and, in particular, to tissue engineering decellularized, allogeneic and xenogeneic, composite tissue bioscaffolds for clinical use as engraftments for musculoskeletal tissue interface reconstruction in the upper and lower extremities, and to methods for producing such bioscaffolds.

BACKGROUND

Mutilating tendon or ligament injuries arising from trauma or disease often require surgical reconstruction or surgical grafts in order to restore function. While autologous sources of tendon and ligament graft material, i.e. tissues that are harvested from the tissue recipient, are sufficient for minor deficits, they are quickly exhausted in cases of extensive tendon or ligament loss (White 1960). Considering that the use of autograft material from non-contiguous donor sites leads to additional operative time and donor site morbidity (Zhang et al., 2003; Zhang et al., 2009), the use of suitable, readily available, effective and safe allografts becomes a desirable target. However, the use of allogeneic graft material in its native form can lead to pronounced immune responses from the host compromising graft integrity and, ultimately, causing graft rejection and/or failure of the reconstruction.

Musculoskeletal interfaces that connect dissimilar tissues such as hard tissue, e.g. bone, and soft tissues, e.g. tendon, ligament, muscle, cartilage, that are crucial in the efficient and smooth load transfer between those tissues to ensure an optimal range of motion and stability, are highly prone to injuries and such injuries are difficult to treat. Because of large differences in the elastic modulus (EM) between soft and hard tissues, reconstruction of the transition zone is difficult and it is believed that even with current surgical techniques, this transition zone is never truly reconstituted (Thomopoulos et al., 2010).

Since healing between tissues of similar elastic moduli results in a stronger interface than between tissues of disparate elastic moduli, it would be highly desirable to have suitable, readily available, effective and safe composite tissue grafts available for immediate use, particularly in cases of extensive tissue interface injuries. The present invention addresses this need.

SUMMARY

One aspect of the present invention is a method of producing a decellularized composite tissue bioscaffold for musculoskeletal tissue interface reconstruction by physico-chemically treating a musculoskeletal tissue interface isolated from allogeneic sources. In certain embodiments, such musculoskeletal tissue interfaces can also be isolated from xenogeneic sources. The method comprises treatment of the interface with detergents, chemical oxidants and ultrasonic energy, and wash steps in between to remove residual detergents as well as oxidants. The resulting bioscaffold may be freeze-dried or lyophilized, sterilized and aseptically packaged for subsequent use.

Another aspect of the present invention is a decellularized, composite tissue bioscaffold for musculoskeletal tissue interface reconstruction, made from natural musculoskeletal tissue interface and produced by the methods described herein, for clinical use as engraftment in upper and lower extremities, including in humans and animals. These natural musculoskeletal tissue interfaces include natural soft tissue-hard tissue interface tissues such as the tendon-bone interface, the ligament-bone, muscle-bone and cartilage-bone. In a further aspect of the present invention, the composite tissue bioscaffold may be seeded prior to engraftment with cells from a graft recipient (human or animal) to improve healing upon engraftment.

In a further aspect of the present invention, methods of treatment using the decellularized composite tissue bioscaffolds for clinical use as engraftments in the upper and lower extremities in humans and animals are provided. In this context, both allogeneic and xenogeneic bioscaffolds are contemplated. Tendon-bone or ligament bone bioscaffolds are embodiments of a composite tissue bioscaffold that are particularly useful for treating tendon or ligament injuries, as they often result from military training or sports injuries involving anterior cruciate ligament (ACL) tears, rotator cuff tears, and Achilles tendon ruptures. Further embodiments such as cartilage-bone bioscaffolds that also include meniscus-bone bioscaffolds find application in meniscus injuries and degenerative processes leading to joint disorders such as arthritis.

The above summary is not intended to include all features and aspects of the present invention nor does it imply that the invention must include all features and aspects discussed in this summary.

BRIEF DESCRIPTION OF THE DRAWINGS

The accompanying drawings illustrate embodiments of the invention and, together with the description, serve to explain the invention. These drawings are offered by way of illustration and not by way of limitation; it is emphasized that the various features of the drawings may not be to-scale.

DEFINITIONS

Figure 1:
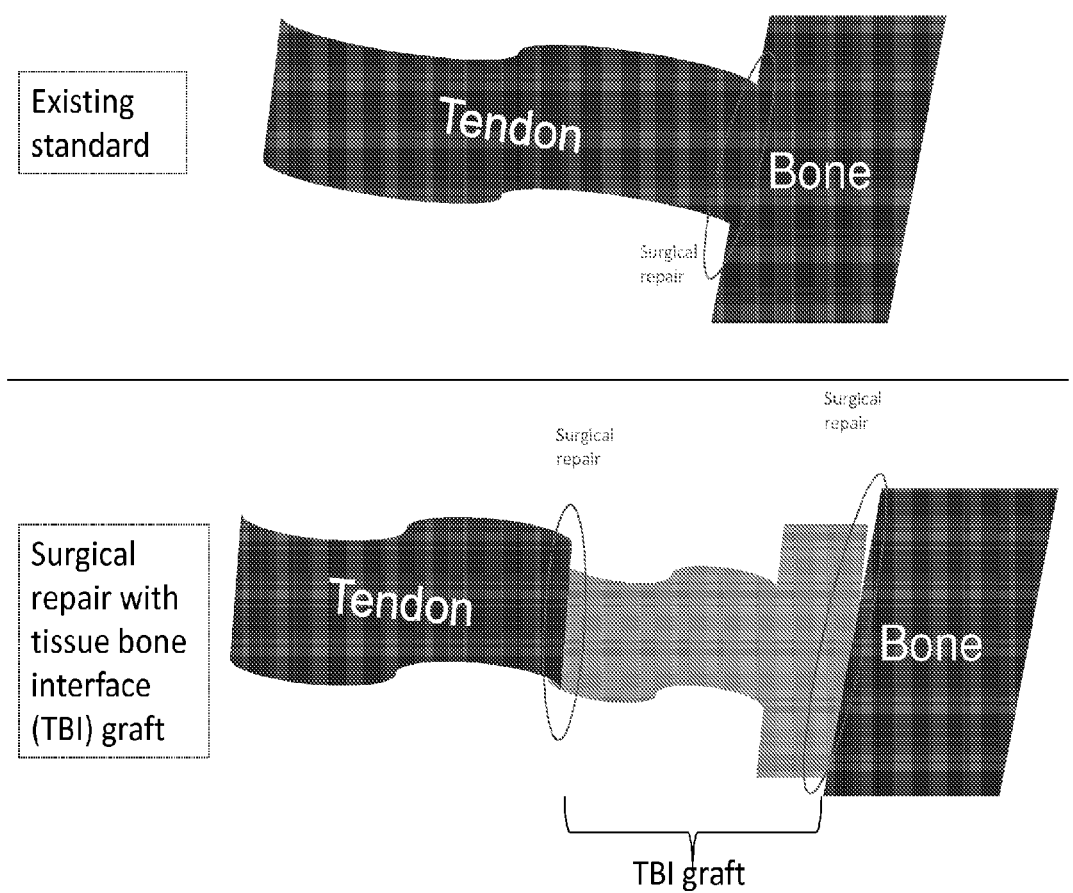
FIG. 1 illustrates schematically the concept of surgical repair using a tissue bone interface (TBI) graft, in comparison to the existing standard. Through the provision of bone-to-bone and tendon-to-tendon healing, the TBI graft facilitates a faster and more robust healing of the injured sites.

Before embodiments of the present disclosure are further described, it shall be understood that this disclosure is not limited to particular embodiments described, as such may, of course, vary. It shall also be understood that the terminology used herein is for the purpose of describing particular embodiments only, and is not intended to be limiting, since the scope of the present disclosure will be limited only by the appended claims.

The practice of the present invention may employ conventional techniques of chemistry, cell biology, immunology, biochemistry, as well as of bone, joint, plastic and reconstructive surgery, which are within the capabilities of a person of ordinary skill in the art. Such techniques are fully explained in the literature. For definitions, terms of art and standard methods known in the art, see, for example, 'Current Protocols in Cell Biology', John Wiley & Sons (2007); 'Human Tendons', by Laszlo Jozsa & Pekka Kannus, Human Kinetics (1997). Each of these general texts is herein incorporated by reference.

Unless defined otherwise, all technical and scientific terms used herein have the same meaning as commonly understood by a person of ordinary skill in the art to which this invention belongs. The following definitions are intended to also include their various grammatical forms, where applicable. As used herein, the singular forms "a" and "the" include plural referents, unless the context clearly dictates otherwise. Thus, for example, reference to "a tissue" includes not only a single tissue, but also a combination of two or more tissues.

A "composite tissue bioscaffold", as used herein, relates to a three-dimensional matrix derived from natural soft tissue-hard tissue interface tissues that supports metabolic activities, provides for unimpeded transport of large macromolecules, provides biomechanical strength for the tissue engineered construct, and permits typical cell type interactions in tissues. These composite tissue bioscaffolds have both clinical and research use. Additives including growth factors such as TGF-beta, VEGF, PDGF, BMPs, NGFs and similar as well as antibiotics may be added during the preparation of a composite tissue bioscaffold to enhance stability and yield of the resulting bioscaffold.

The expressions "natural soft tissue-hard tissue interface", "musculoskeletal tissue interface" and "composite tissues" are used interchangeably herein. Natural soft tissue-hard tissue interfaces, musculoskeletal tissue interfaces or composite tissues are tissues that can be isolated directly from, preferably, human sources or animal sources. Such tissues interfaces or composite tissues include, but are not limited to, tendon-bone, ligament-bone, cartilage-bone including meniscus-bone and muscle-bone. If the composite tissues are isolated from one human and grafted to another human, they are considered "allogeneic", i.e., derived from a non-genetically identical member of the same species. It is also contemplated to obtain composite tissues from animal sources for use in the methods of the present invention. If the composite tissues are isolated from animal sources, they are considered "xenogeneic", i.e., from a member of a different species. In either case, soft tissue-hard tissue interface tissues are obtained from a fresh-frozen cadaveric donor. To obtain musculoskeletal tissue interfaces from a cadaveric donor, standard biopsy techniques known in the art may be employed.

"Donor", as used herein, refers to a mammalian cadaveric source, preferably a deceased human, of tissues or cells.

"Recipient", as used herein, refers to a mammal, preferably a human, who receives tissues or cells by implantation or grafting.

"Tissue", as used herein, refers to all parts of a body formed by cells.

"Grafting", as used herein, refers to the implantation of a composite-tissue bioscaffold, into an animal or human, with or without prior in-vitro seeding of cells of the graft recipient.

"Physicochemical treatment", as used herein, refers to a combined application of methods involving ultrasonication, chemical and oxidizing treatment.

"Decellularization", as used herein, refers to the substantial (at least 75%), nearly complete (at least 95%) or complete removal of cellular components of musculoskeletal tissue by the use of physical, chemical, or ultrasonic means, or any combination thereof. The remaining decellularized musculoskeletal tissues comprise the extracellular matrices of the native musculoskeletal tissues and tissue interfaces. In some embodiments of the invention the decellularization process removes at least 75% of the cells. In some embodiments of the invention the decellularization process removes at least 80% of the cells, at least 85%, at least 90%, at least 95%, at least 96%, at least 97%, at least 98%, at least 99% or all of the cells are removed. As described in the Experimental Procedures and Examples, the level of ultrasonication energy that is applied in the course of the decellularization process contributes in achieving a high degree of decellularization, while preserving the biomechanical properties of the tissues and tissue interface. It is understood that it is not necessarily preferred to achieve a maximally possible decellularization, if doing so negatively affects the biomechanical properties of the tissues and tissue interface. The optimum degree of decellularization will depend upon the properties of the tissue interface and its intended use.

"Detergent", as used herein, refers to any compound or composition that is capable of solubilizing and extracting lipids from a musculoskeletal tissue. Examples of detergents that may be utilized in accordance with the present invention include, but are not limited to, Triton X-100, sodium dodecyl sulfate (SDS), sodium lauryl sulfate (SLS), or any other detergent or combination thereof known to one of ordinary skill in the art.

"Low-level ultrasonication", as used herein, means the treatment of a musculoskeletal tissue with ultrasonic waves to aid disintegration of cells and decellularization in general by transfer of mechanical energy to tissue particles for a certain amount of time, which can last from several seconds to several minutes. For low-level ultrasonication ultrasonic energy between 1 and 10 kW is applied or as specified in the method description in the Examples.

"High-level ultrasonication", as used herein, means the treatment of a musculoskeletal tissue with ultrasonic waves to aid disintegration of cells and decellularization in general by transfer of mechanical energy to tissue particles for a certain amount of time, which can last from several seconds to several minutes. For high-level ultrasonic energy higher than 10 kW is applied or as specified in the method description in the Examples.

"Sample", as used herein, relates to a mixture of musculoskeletal tissue, typically, although not necessarily, in fluid form, e.g., in water or in solvent. A sample for ultrasonication can size from several microliters, milliliters, deciliters or liters.

DETAILED DESCRIPTION OF THE EMBODIMENTS

As summarized above, decellularized, allogeneic or xenogeneic composite tissue bioscaffolds for clinical use as engraftments in the upper and lower extremities and methods for producing such bioscaffolds are provided. Such decellularized composite tissue bioscaffolds may be engineered from natural soft tissue-hard tissue interface tissues such as ligament-bone or tendon-bone interfaces by means of physicochemical treatments. Methods to produce such composite tissue bioscaffolds include treatment of the soft tissue-hard tissue interface with detergents, oxidants and ultrasonic energy, and wash steps inbetween to remove residual detergents and/or oxidants. The resulting bioscaffold can then be freeze-dried or lyophilized, sterilized and aseptically packaged for subsequent use.

Interfaces that connect dissimilar tissues such as hard tissue, e.g. bone, and soft tissues, e.g. tendon, ligament, muscle, cartilage, are extremely difficult to reconstruct upon injury. The disclosed composite tissue bioscaffolds, particularly tendon-bone, ligament-bone, bone-ligament-bone, bone-tendon-bone, have been demonstrated to retain most of their native biomechanical integrity, and allow improved healing and earlier mobilization due to the provided benefit of bone-to-bone healing.

The use of tissue engineered composite constructs that comprise hard tissue plus soft tissue, for example bone plus tendon or bone plus ligament, allows reconstruction with bone-to-bone healing, thus creating stronger junctions at an earlier time point than when single-tissue, non-composite tendon or ligament are used.

However, so far it has not been possible to obtain sufficiently acellularized soft tissue-hard tissue interfaces that would be feasible for engraftment into a human without evoking an immune response great enough to jeopardize successful grafting of a bio scaffold. The use of allogeneic or xenogeneic graft material in its native form leads to pronounced immune response from the host. This immune response compromises graft integrity and, ultimately, leads to failure of the reconstructive effort.

The inventors were able to devise a physicochemical treatment procedure of soft tissue-hard tissue interfaces that resulted in nearly (at least 90% cell removal) or completely decellularized bioscaffolds which maintained biomechanical properties similar to the respective native tissues and which can be used clinically for engraftment in humans and animals following soft tissue-hard tissue interface injuries.

Human Tendons

In some embodiments, tendon-bone interface or tendon-bone composite tissue bioscaffolds may be used for the repair of injuries of the tendon-bone interface.

Human tendons are strong bands of fibrous connective tissue that connect muscle to bone and are composed of arrays of collagen fibers (mostly type 1 collagen) and elastin embedded in a proteoglycan-water matrix. The point of connection between muscle and tendon is the myotendinous junction, while the point of connection between tendon and bone is the osteotendinous junction. Most muscles have a single tendon distally, although some muscles have both a proximal and distal tendon. The basic functions of tendons, which are typically classified as flexors (flexing or bending a joint) or extensors (extending or straightening a joint) are to withstand tension and to allow transmission of forces created in the muscle to the bone, thus making joint and limb movements possible (Sharma & Maffulli, 2005; Kannus, 2000). This is made possible by a complex macro- and microstructure of tendons and tendon fibers, where collagen is arranged in hierarchical levels of increasing complexity, beginning with tropocollagen, a triple-helix polypeptide chain, which unites into fibrils; fibers (primary bundles); fascicles (secondary bundles); tertiary bundles; and the tendon itself. Soluble tropocollagen molecules form cross-links to create insoluble collagen molecules, which aggregate to form collagen fibrils. A collagen fiber is the smallest tendon unit that can be tested mechanically and is visible under light microscopy. Although collagen fibers are mainly oriented longitudinally, fibers also run transversely and horizontally, forming spirals and plaits (Sharma & Maffulli, 2005).

Healthy tendons have a fibro-elastic texture and show strong resistance to mechanical challenges. During various phases of movement, tendons are exposed to longitudinal as well as transversal and rotational forces, whereby the complex three-dimensional architecture of tendons provides critical support to prevent damage and disconnection of fibers. Muscles designed to create powerful, resistive forces such as the quadriceps and triceps brachii muscles, have short and broad tendons, while those that have to carry out subtle and delicate movements, like the finger flexor tendons, have long and thin tendons (Kannus, 2000). Intrasynovial tendons of the hand and the feet are surrounded by tendon sheaths or similar networks of connective tissue that contain the vascular, lymphatic and nerve supply to the tendon and whose main function is to minimize the friction between the tendon and its surroundings. Since proper movement and gliding of the tendon determines its efficiency, the tendon needs to be able to move freely and in an uninhibited manner. Tendon sheaths have two layers, an outer, fibrotic sheath, which consists of collagen fibrils and fibers, as well as an inner, synovial sheath, which consists of two sheets of synovial lining cells. These lining cells contain a thin film of fluid which is similar to the composition of the synovial fluid of a joint and which improves lubrication. The synovial lining cells are covered with fine collagen fibrils ('Human Tendons', by Laszlo Jozsa & Pekka Kannus, Human Kinetics (1997)). Synovial tendon sheaths are found in areas that often experience increased mechanical stress such as tendons of the hands and feet, where efficient lubrication is important (Sharma & Maffulli, 2006).

The extracellular tendon matrix consists of collagen fibers, elastic fibers, ground substance and inorganic components such as copper, manganese and calcium. The tendinous ground substance, which surrounds the collagen, consists of macromolecules such as proteoglycans and glycosaminoglycans (GAGs), structural glycoproteins, and a wide variety of other smaller molecules. The proteoglycans and glycosaminoglycans have a considerable capacity to bind water and are important for the biomechanical properties of tendon against shear and compressive forces.

Tendon Structure.

Tenoblasts and tenocytes lie between the collagen fibers along the axis of tendon and are its major cellular components. Tenoblasts are immature tenocytes with higher metabolic rates that eventually mature into tenocytes. Chondrocytes are located at the sites of attachment and insertion into bone. Synovial cells of the tendon sheath as well as vascular cells form the remaining cellular components of a tendon. Tendons receive their blood supply from blood vessels entering from the myotendinous and osteotendinous junctions, the intratendinous vascular network and the synovial sheath.

Tenocytes synthesize collagen and all components of the extracellular matrix and are active in energy production, which can be aerobic as well as anaerobic. Compared to skeletal muscles, tendons and ligaments have a low metabolic rate, low oxygen consumption and a fairly well developed anaerobic energy production capacity. On the upside, a low metabolic rate allows tendons to maintain tension for prolonged periods without becoming ischemic and necrotic. On the downside, a low metabolic rate means that tendon injuries take a long time to heal.

Tendon Biomechanics.

Tendons transmit force from muscle to bone, while at the same time acting as a buffer by absorbing external forces to limit tearing and other damage to the muscle. As a consequence, tendons have, by necessity, to exhibit high mechanical strength, good flexibility and high elasticity. The biomechanical properties of tendons are dependent on the collagen fiber diameter, fiber orientation, and collagen content. Tendons subject to multidirectional forces display collagen fiber bundles that lack regular orientation and the connective tissue is irregularly arranged. In contrast, tendons subject to unidirectional strain display collagen fiber bundles with mostly parallel orientation. The mechanical behavior of collagen depends on the number and types of intra- and intermolecular bonds. The tensile strength of a tendon is a function of its thickness and its collagen content. The biomechanical properties of an isolated tendon are tested in in vitro tensile tests. Test parameters that can be inferred from such tensile testing include stiffness, maximum load, and strain to maximal load. For the testing, the tendon tissue is elongated at a set rate, while the changes in force are recorded. The force is then plotted against displacement. Methods for testing of biomechanical properties include compression and tension testing.

Tendon-Bone Interfaces in the Upper and Lower Extremities as Potential Allogeneic Sources.

The basic functions of tendons are to withstand tension and to allow transmission of forces created in the muscle to the bone, thus making joint and limb movements possible (Sharma & Maffulli, 2005; Kannus, 2000). Tendons are generally classified as flexor tendons (involved in flexing a joint) or extensor tendons (involved in extending a joint);

some tendons, such as the semitendinosus tendon (hamstring) can function as a flexor of one joint and an extensor of another.

In accordance with embodiments of the present invention, allogeneic tendon-bone interface tissues can be sourced from cadaveric flexor or extensor tendons in the upper or lower extremities and that can be utilized as composite tissue allografts for tendon as well as ligament reconstruction in the upper or lower extremities. Apart from tendon and ligament reconstruction, allogeneic flexor or extensor composite tissue tendon bioscaffolds might be suitable for joint reconstruction, muscle reinforcement and pelvic floor reconstruction.

Tendons in the Upper Extremities

Finger Flexor Tendons.

Flexor pollicis longus tendon, flexor digitorum superficialis tendons and flexor digitorum profundus tendons belong to the group of finger flexor tendons. Flexor Tendons of the Lower Arm. Flexor carpi radialis tendon, palmaris longus tendon, flexor carpi ulnaris tendon and the common flexor tendon are flexor tendons of the forearm. The common flexor tendon is a tendon shared by a number of superficial flexor muscles in the forearm and attaches to the medial epicondyle of the humerus. It serves as the origin for a number of superficial muscles of the anterior compartment of the forearm such as the palmaris longus (a small tendon between the flexor carpi radialis and the flexor carpi ulnaris) or flexor digitorum superficialis (an extrinsic flexor muscle of the fingers at the proximal interphalangeal joints). The flexor digitorum profundus is another muscle in the forearm that flexes the fingers. It is an extrinsic hand muscle because it acts on the hand, while its muscle is located in the forearm and is a flexor of the wrist, midcarpal, metacarpophalangeal and interphalangeal joints.

Finger Extensor Tendons.

Extensor digiti minimi tendon, extensor digitorum communis tendons, extensor indicis tendon, extensor pollicis brevis tendon and extensor pollicis longus tendon belong to the group of finger extensor tendons. The abductor pollicis longus tendon, also found in the extensor group, is included in this category.

Flexor Tendons of the Arm and Shoulder.

The tendons of the rotator cuff muscles help stabilize the shoulder, while the biceps tendon helps to bend the elbow and rotate the arm.

Extensor Tendons of the Forearm.

Extensor carpi ulnaris tendon; Extensor carpi radialis brevis tendon, extensor carpi radialis longus tendon and the common extensor tendon are extensor tendons of the forearm.

Tendons in the Lower Extremities

The Achilles tendon (also called Tendocalcaneus) is part of the posterior leg and is the thickest and strongest tendon in the body. It connects the superficial muscles of the posterior leg, plantaris, soleus and gastrocnemius (calf muscle) to the calcaneus (heel) bone.

Flexor Tendons of the Thigh.

The semitendinosis tendon, gracilis tendon, semimembranosis tendon are flexor tendons of the thigh. Semitendinosus is one of the hamstring muscles and functions both as flexor and extensor by helping to extend the hip joint and to flex the knee joint; it also helps to medially rotate the knee.

Flexor Tendons of the Leg.

Flexor digitorum longus tendons, flexor hallucis longus tendons, and tibialis posterior tendon are flexor tendons of the leg. Flexor digitorum longus, one of the muscles of the posterior compartment of the leg, functions to curl the toes and to stabilize the lower leg, while flexor hallucis longus, another muscle of the posterior compartment, performs plantar flexion of the big toe alone (downward movement of the toes). Tibialis anterior is situated on the lateral side of the tibia; it is thick, fleshy above, tendinous below and acts to dorsiflex (turn upward) and invert the foot. Tibialis posterior, a muscle of the posterior compartment of the leg, is the main stabilizing muscle of the lower leg and assists with foot inversion and ankle plantar flexion. Peroneus longus, and peroneus brevis are everters of the foot that secondarily plantarflex at the ankle.

Flexor Tendons of the Foot.

The flexor digitorum longus and brevis, flexor hallucis longus and brevis, and flexor digiti minimi brevis tendon are flexor tendons of the foot.

Extensor Tendons of the Leg.

Extensor digitorum longus tendons and extensor hallucis longus tendon are extensor tendons of the leg. The extensor digitorum longus tendons are located at the lateral part of the front leg and act to dorsiflex the foot as well as the toes and invert the foot. The extensor hallucis longus is part of the anterior leg and functions to extend the big toe, dorsiflex the foot, and assists with foot inversion. Tibialis anterior and peroneus tertius are extensor tendons of the leg that dorsiflex the foot at the ankle.

Extensor Tendons of the Foot.

Extensor digitorum longus and brevis tendons as well as extensor hallucis longus and brevis tendons are extensor tendons of the foot. The extensor digitorum brevis is a muscle on the dorsal (upper) part of the foot that functions to extend the smaller toes, while the extensor hallucis brevis, which is a muscle of the dorsum of the foot, acts to extend the big toe.

Tendon Injuries and Problems in Tendon Repair

Tendon injuries can be acute strain injuries or ruptures of the muscle-tendon units or chronic injuries due to tendon overuse without proper recovery time between use. Tendon injuries are most often acquired during sports and exercise and heal in several phases. After the initial inflammatory phase within the first 24-72 hours, the remodeling phase begins within an increased collagen synthesis. After approximately six weeks, the modeling stage begins with high collagen synthesis and high tenocyte metabolism, in the course of which the injured tissue changes from cellular to fibrous and eventually to scar-like tissue.

Intrasynovial tendons heal by intrinsic healing, leaving minimal scarring, whereas extrasynovial tendons heal through the formation of vascularized adhesions that ultimately impair tendon gliding and function. Tendon injuries, whether incurred through acute trauma (such as tendon rupture) or chronic overuse can cause significant disability followed by a protracted convalescent period.

Allogeneic Tendon-Bone Bioscaffolds for Engraftment

In accordance with embodiments of the present invention, allogeneic tendon-bone bioscaffolds are described that can be sourced from cadaveric flexor or extensor tendons in the upper or lower extremities and that can be utilized as allografts for tendon as well as ligament reconstruction, and beyond, in the upper or lower extremities. Such allogeneic tendon-bone bioscaffolds can clinically be used in the acellularized or reseeded state.

Acellularized Allogeneic Tendon-Bone Bioscaffolds.

The substantial removal of cellular elements in an allogeneic tendon-bone interface considerably lowers immunogenicity and the risk of infection upon grafting of an allogeneic tendon-bone bioscaffold.

Reseeding of Acellularized Tendon-Bone Bioscaffolds.

Acellularized tendon-bone bioscaffolds provide strong grafts, but the healing process can be slow since it requires the in-migration of the graft recipient's fibroblasts into the graft. Reseeding may accelerate healing by populating these grafts with cells from the graft recipient prior to implantation.

Reseeding Before Implantation.

Prior to implantation into a graft recipient, complete cell-tendon-bone constructs can be created by reseeding previously acellularized tendon-bone bioscaffolds with cells, including tenocytes, fibroblasts, or adult mesenchymal stem cells, whether adipose- or bone marrow-derived. These cells can be harvested prior to grafting of the construct from the graft recipient. They may or may not then be expanded in culture and then re-seeded onto the acellularized tendon scaffold. Although tenocytes and tenoblasts are the natural cellular inhabitants of tendon, they have limited seed potential, because they undergo a phenotypic drift after 2-3 passages in culture (Bagnaninchi et al., 2007b). Furthermore, the cell yield at an open biopsy (or first stage tenolysis) can be low relative to the amount of tendon material obtained (Yao et al., 2006), and tenocytes generally proliferate slower than fibroblasts (Khan et al., 1998; Kryger et al., 2007; and Klein et al., 2001).

Human Ligaments

In some embodiments, ligament-bone interface or ligament-bone composite tissue bioscaffolds may be used for the repair of injuries of the ligament-bone interface.

Human ligaments, similar to tendons, are strong bands of fibrous connective tissue consisting of fibers made mainly out of type 1 collagen. In contrast to tendons, which connect muscle to bone, ligaments connect bones to other bones across a joint. Some ligaments limit the mobility of a joint or prevent certain movements altogether. Ligaments are elastic and lengthen under tension, unlike tendons, which are inelastic.

Capsular ligaments are part of the articular capsule that surrounds synovial joints. They act as mechanical reinforcements. Extra-capsular ligaments provide joint stability. Intra-capsular ligaments, also provide stability, but permit a far larger range of motion. Cruciate ligaments occur in pairs (anterior and posterior).

Ligaments of the Head, Neck, and Chest

Ligaments of the head, neck and chest, include the cricothyroid ligament, periodontal ligament and suspensory ligament of the lens, which all are ligaments of the head and neck, while the suspensory ligament of the breast is a ligament of the human thorax.

Ligaments of the Upper Extremities

The radial and ulnar collateral ligaments of the interphalangeal and metacarpophalangeal joints are ligaments of the human hand. The palmar radiocarpal ligament, dorsal radiocarpal ligament, ulnar collateral ligament and radial collateral ligament are ligaments of the human wrist. The acromioclavicular ligaments surround and support the acromioclavicular joint which is the connection between the scapula and the clavicle. The coracoclavicular ligaments hold the clavicle down by attaching it to a bony knob on the scapula called the coracoid process.

The scapholunate interosseous ligament is a broad ligament connecting the scaphoid bone to the lunate bone.

Ligaments in the Lower Extremities

Ligaments of the lower extremities include the anterior cruciate ligament (ACL), lateral collateral ligament (LCL), posterior cruciate ligament (PCL), medial collateral ligament (MCL), which all are main ligaments of the human knee. In the quadruped from, the ACL is referred to as the cranial cruciate ligament (CrCL), while the PCL is referred to as the caudal cruciate ligament (CaCL).

Ligaments of the Pelvis

The anterior sacroiliac ligament, the posterior sacroiliac ligament, the sacrotuberous ligament, the sacrospinous ligament, the inferior pubic ligament, the superior pubic ligament and the suspensory ligament of the penis are ligaments of the human pelvis.

Ligament Injuries and Problem in Ligament Repair

Ligament injuries, which are often acquired during weight-bearing sports activities such as downhill skiing, running, jumping and the like, can lead to instability of the joint that the ligament is supposed to stabilize. Instability of a joint can lead to cartilage wear over time and eventually to osteoarthritis. Therefore ligament injuries need to be taken seriously and repaired.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. In the following, experimental procedures and examples will be described to illustrate parts of the invention.

General Experimental Procedures

In preferred embodiments, the bioscaffolds were decellularized using a combination of low or high power ultrasonication, detergents and chemical to effectively remove extracellular matrix materials and to increase the average pore size by changing, e.g., oxidant concentration, level and/or length of ultrasonication. Preferred oxidants include hydrogen peroxide and peracetic acid and preferred detergents include sodium dodecyl sulfate (SDS); the oxidant can be added sequentially or simultaneously with the detergent. Typical oxidant concentrations range from 1, 1.5, 2 or 3 to 10, 20, 30, up to 50% (w/v) and will vary depending on the starting density of the tissue. Residual chemicals may be removed by repeated washes with distilled water. The bioscaffold may be freeze-dried, sterilized and aseptically packaged in accordance with standard techniques in the art prior to use.

The added step of ultrasonication, in varying levels of energy and length of time, proved critical in achieving a very high degree of decellularization (at least 75%, usually at least 95%) and, thus, minimizing the bioscaffold's immunogenic potential in the graft recipient upon implantation. The various procedures of biomechanical testing, particularly testing of ultimate strength, stiffness and displacement to failure, confirmed to evaluate the retention of the native biomechanical properties and the suitability of the bioscaffolds for clinical grafting. The described procedures will decrease the time necessary for cellular repopulation and biomechanical integration of the bioscaffolds in vivo.

EXAMPLES

The following examples are put forth so as to provide those of ordinary skill in the art with a complete disclosure and description of how to make and use the present invention; they are not intended to limit the scope of what the inventors regard as their invention. Unless indicated otherwise, part are parts by weight, molecular weight is average molecular weight, temperature is in degrees Centigrade, and pressure is at or near atmospheric.

Example 1: Physicochemical Decellularization of Human Tendon-Bone Interface for Producing Decellularized, Allogeneic Soft Tissue-Hard Tissue Interface Bioscaffolds Tendon-bone and ligament-bone interfaces (collectively termed TBI) represent the interface between tissues of different stiffness, and connect tendinous soft tissue (tensile modulus≈200 MPa) to bony hard tissue (tensile modulus≈20 GPa) (Thomopoulos et al., 2010).

Injuries at the TBI are difficult to address. Standard techniques of reattachment using suture anchors or through drill-holes in bone lead to diminished strength. In essence, the original interface is never truly reconstituted. Instead of repair, reconstruction with a TBI graft might allow for more robust bone-to-bone and tendon-to-tendon healing, as schematically illustrated in FIG. 1. For clinical use, TBI grafts must be decellularized to reduce immunogenicity and infectivity. The TBI represents a transition zone comprising four different tissues, namely tendon, fibrocartilage, calcified fibrocartilage, and bone, rendering decellularization challenging.

Tissue Harvest.

Flexor digitorum profundus (FDP) tendons with attached distal phalanx (P3; tissue bone interface constructs) were harvested from human cadaver forearms (Science Care, Phoenix, Ariz.). The constructs were then stored in PBS at −70° C. until further use. The extensor digitorum communis (EDC) tendon was sharply transected at its insertion, the finger pulp, nail plate and nail bed, as well as surrounding skin, and soft tissue and articular cartilage at the P3 base were removed.

Mechanical Preparation.

The constructs were thawed to room temperature and then further prepared by careful and thorough removal of the volar plate, decortication of the dorsal P3 cortex to expose trabecular bone, and transection of the tendon 5 mm proximal to the DP insertion.

Decellularization. The construct samples were randomized to one of three groups. Group 1 (control group) served as an untreated control. Group 2 (chemical decellularization, EDTA-SDS group) underwent chemical decellularization treatment alone comprising 5% peracetic acid (PAA, titrated to pH 7 with 10N NaOH), 0.1% EDTA for four hours with 3 changes of EDTA in this period, followed by a detergent cycle comprising 0.1% SDS in 0.1% EDTA solution for 24 hours with three changes of solution during this period. Group 3 (low power physicochemical decellularization, LPUS-PAA-EDTA-SDS group) underwent low power ultrasonication treatment first. The sample was attached to a styrofoam platform and the ultrasonication probe (VC 505, Sonics & Materials, Newtown, Conn.) was suspended vertically in chilled saline 0.5 cm above the platform-attached sample. Ultrasonication amplitude settings were fixed 100% amplitude, with pulse settings of 3 s on, 1 s off pulses for treatment time of 3 min (22,274 J, 126 W). Ultrasonicated samples then underwent chemical decellularization treatment, as described above for Group 2.

Group 4 (high power physicochemical decellularization, HPUS-PAA-EDTA-SDS group) underwent high power ultrasonication followed by chemical decellularization. Ultrasonication settings were 100% amplitude, pulse settings of 59 s on, 3 s off, for 10 min (88,490 J, 155 W). The chemical decellularization step was identical to Groups 2 and 3. Samples from all groups were fixed in 10% formalin, embedded in paraffin. Sections were cut at 6-8 μm and stained with Harris hematoxylin and eosin, SYTOgreen nucleic acid stain and major histocompatibility complex I (MHC-I) stains.

Methods.

Figure 2:
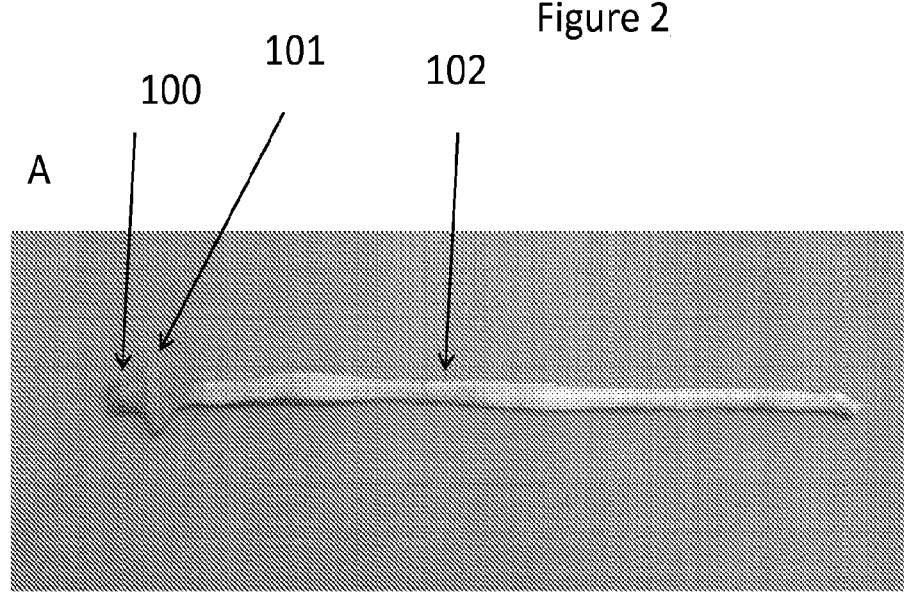
FIG. 2a depicts a tissue bone interface (TBI) construct in its entirety prior to mechanical preparation and decellularization: 100 illustrates the bone part, 102 the tendon part and 101 the transition zone between bone and tendon.
FIG. 2b depicts the dorsal surface of the trimmed, ready to be used for grafting, TBI construct, with the transition zone intact. 103 illustrates the bone side that, upon grafting into a recipient, enables bone-to-bone healing, and 104 illustrates the tendon side that enables tendon-to-tendon healing.
FIG. 2c depicts the volar surface of the same trimmed construct.
Figure 2:
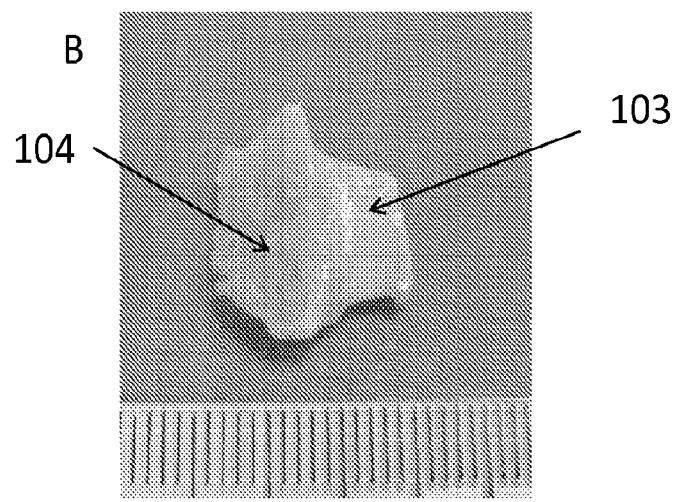
Figure 2:
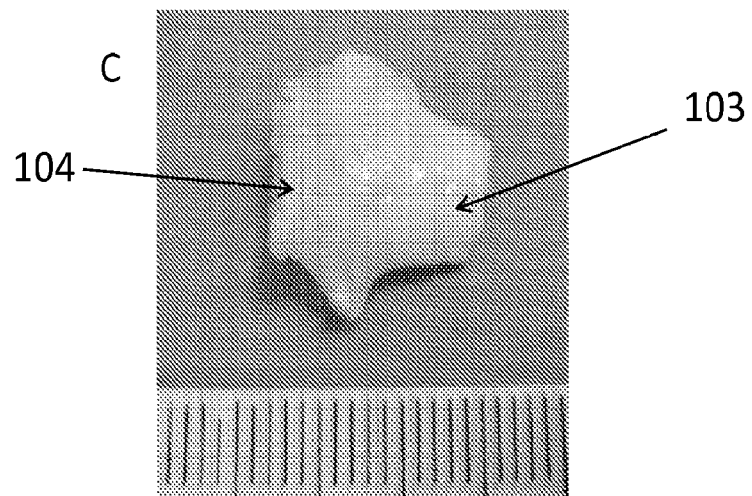
Figure 3:
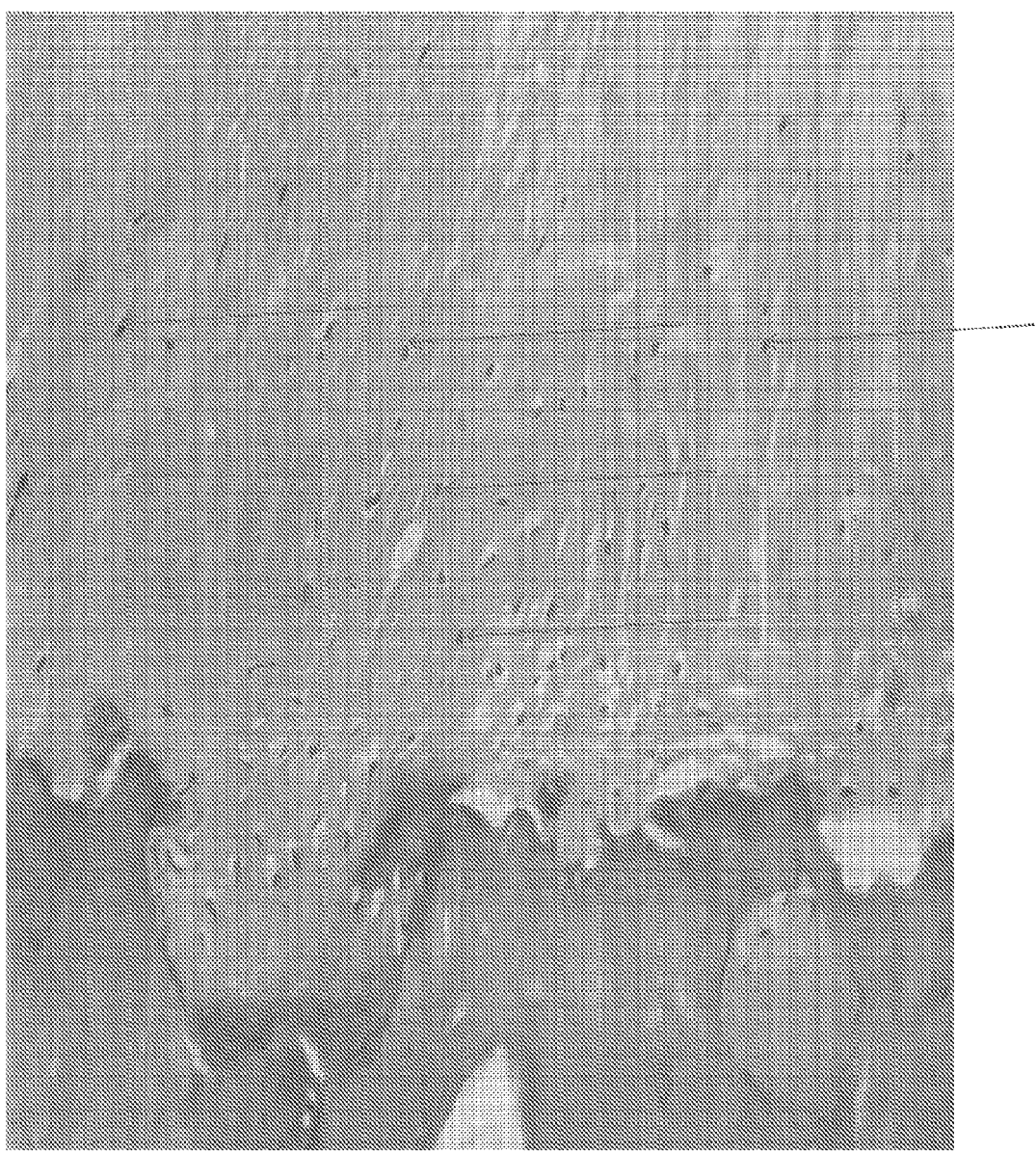
FIG. 3 shows the transition zone histology of TBI constructs ("Group 1") that were left untreated, i.e. that did not undergo physicochemical treatment or ultrasonication. Cells are clearly visible (see arrows).
Figure 6:
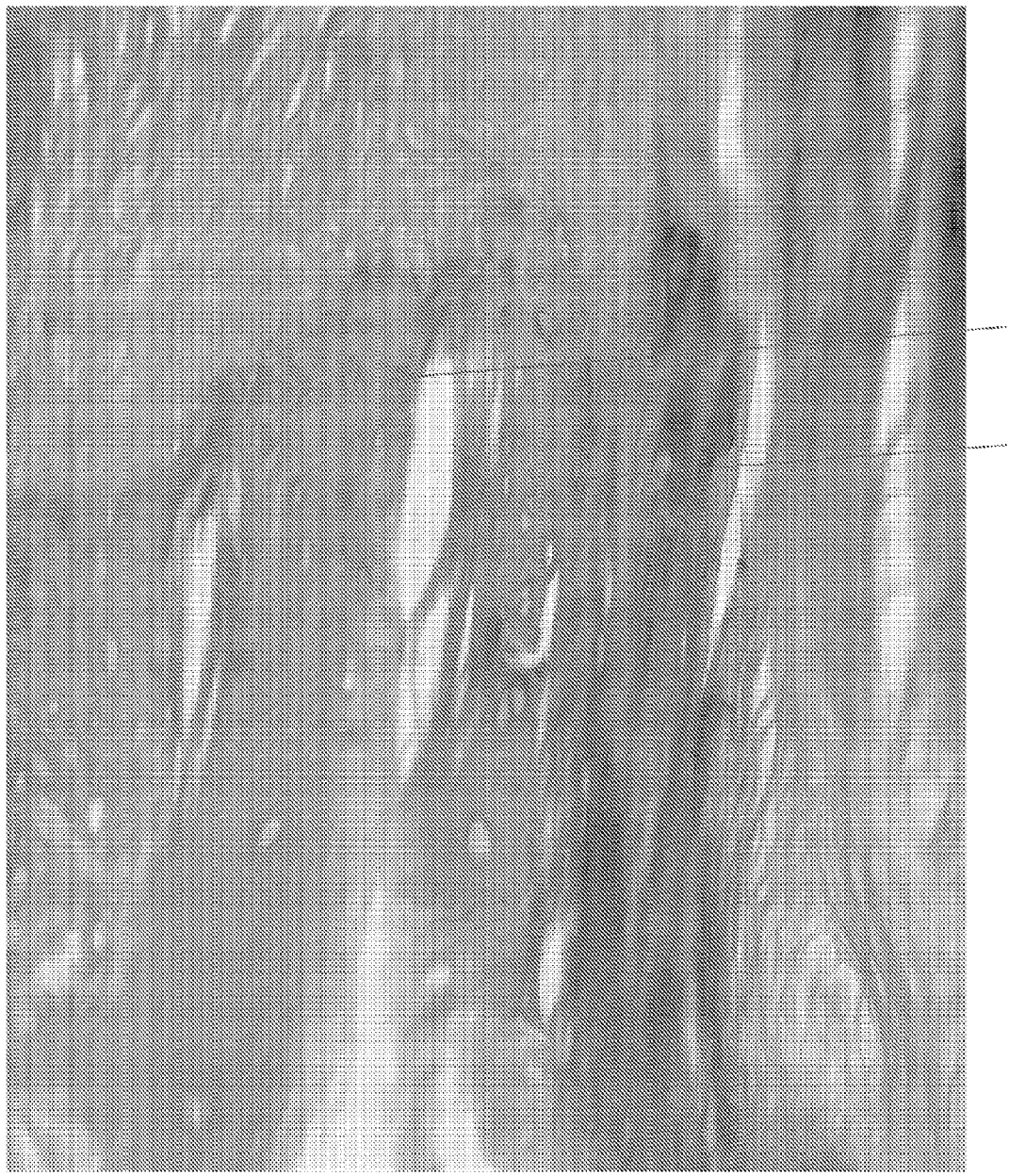
FIG. 6 shows the transition zone histology of TBI constructs ("Group 4") that were decellularized using a high level of ultrasonication energy in addition to detergents and chemical oxidants. In this group, there was, thus, more ultrasonication energy delivered than with Group 3. Compared with Group 3 (FIG. 5), there is also further improvement in extraction of cellular material with almost no cells remaining (cells are indicated with arrows).
Figure 11:
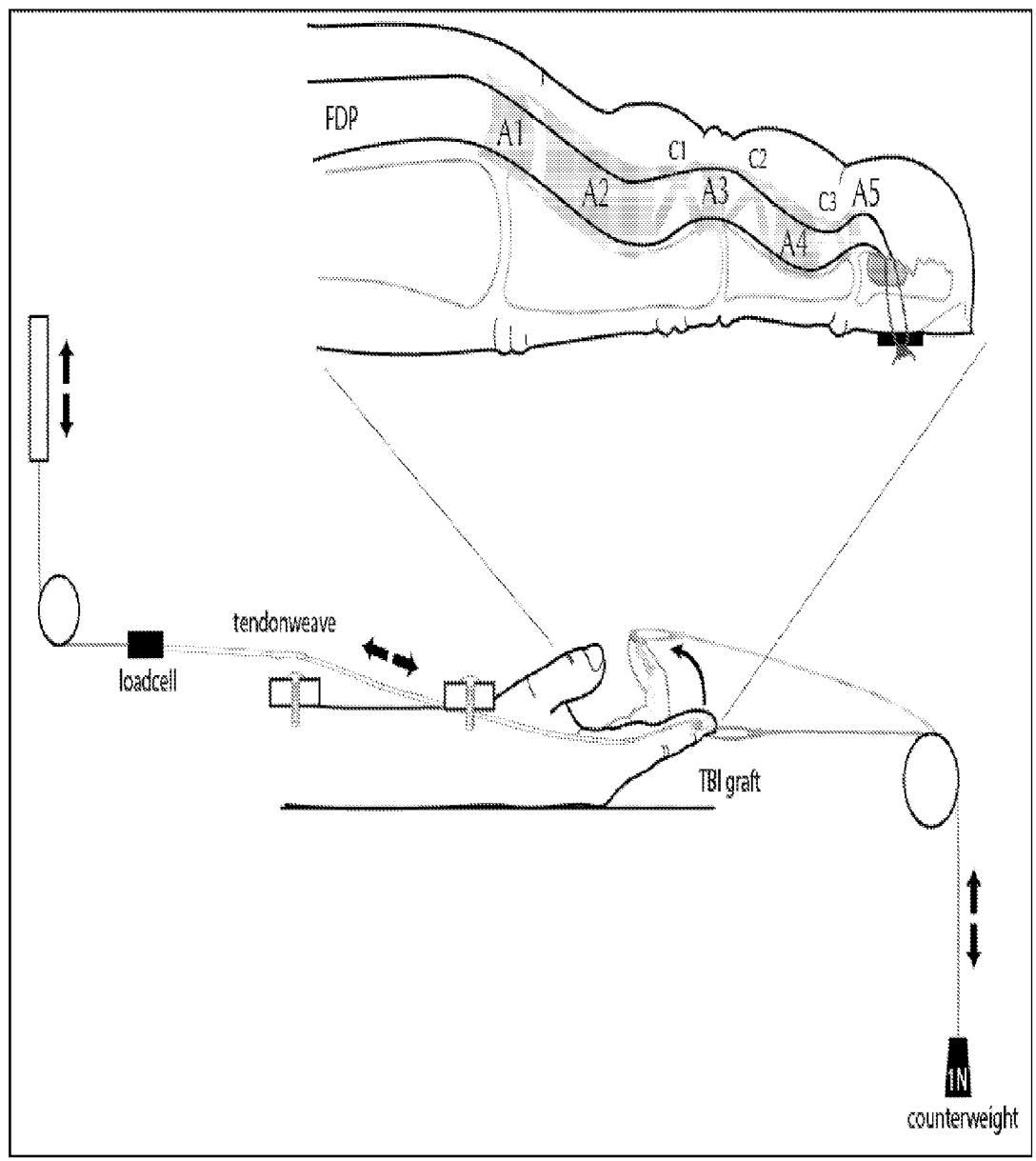
FIG. 11 illustrates a materials test system (MTS) apparatus and method to investigate the tensile strength and motion of human tendon-bone interface (TBI) grafts during finger flexion. An MTS is used to pull the graft to failure after 50 cycles at 7.5N. A 1N counterweight is used to extend the digit between cycles. The annular pulley system is maintained during harvest and replant to assure physiologic motion of the tendon.
Figure 12:
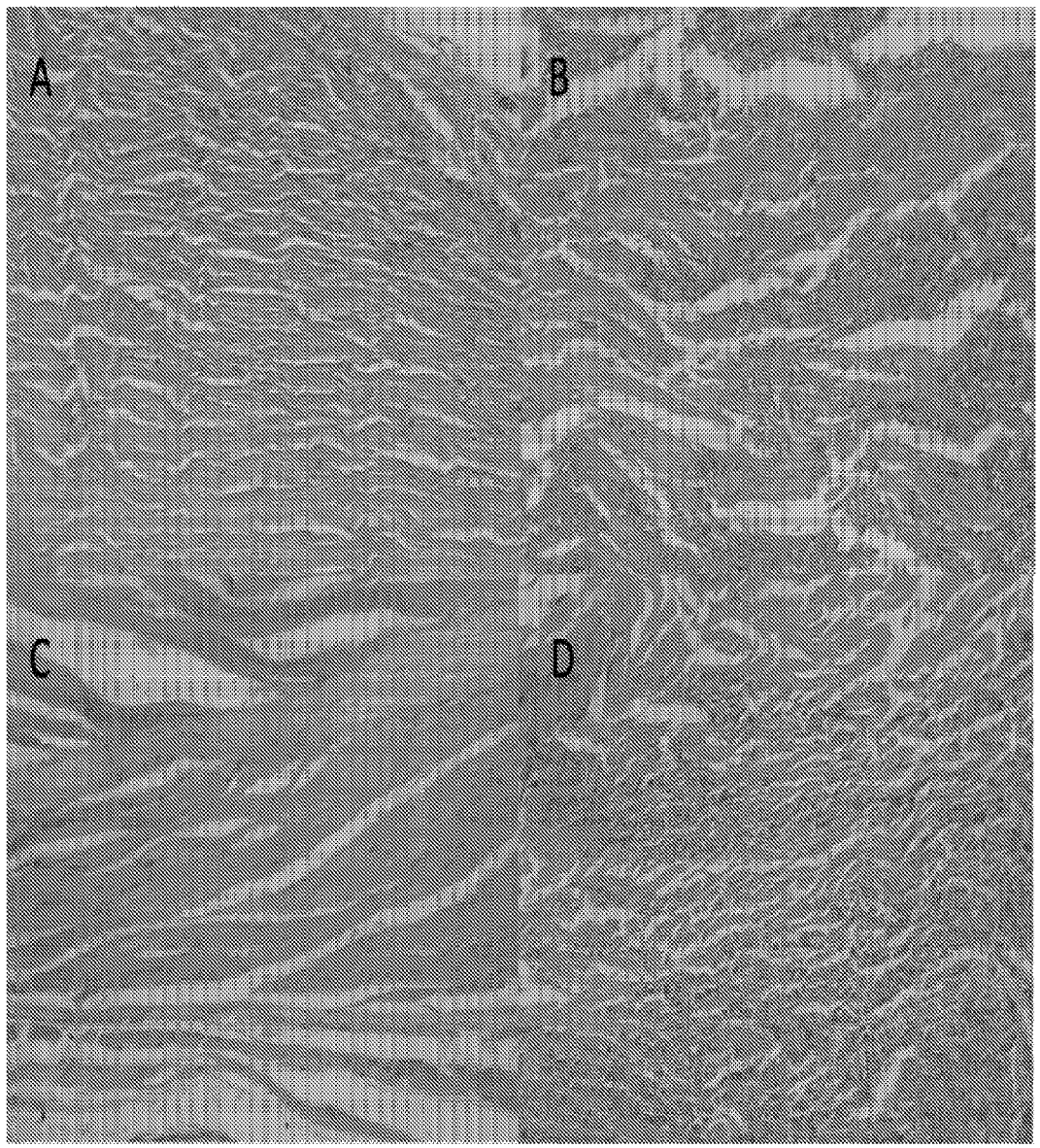
FIG. 12 illustrates H&E staining (20×) showing, on top, tendon substance of the decellularized graft (A) and untreated graft (B) at 2 weeks and, on the bottom, the decellularized graft (C) and untreated graft (D) at 4 weeks following reconstruction. Host cell infiltration is visible in the decellularized grafts (A, C). Donor cell persistence is visible in the untreated grafts (B, D). The decellularization was carried out with high level of ultrasonication.

Human flexor digitorum profundus tendons with attached distal phalanx were harvested from cadavers and divided into four groups (FIG. 2). Group 1 (controls) scaffolds went untreated. Group 2 (decellularization with detergents and chemical oxidants only) scaffolds were treated with 5% peracetic acid, 0.1% ethylenediaminetetraactic acid and 0.1% sodium dodecyl sulfate. Group 3 (low level ultrasonication) scaffolds underwent targeted ultrasonication for 3 minutes (3 sec on, 1 sec off, 22,274 J, 126 W) followed by chemical decellularization (as per Group 2). Group 4 (high level ultrasonication) scaffolds underwent targeted ultrasonication for 10 minutes (59 sec on, 3 sec off, 88,490 J, 155 W) followed by chemical decellularization (as per Group 2). Samples in Groups 3 and 4 were first attached to a foam platform with the volar surface up. The ultrasonication probe (VC505, Sonics and Materials) was suspended in chilled water, 0.5 cm directly above the TBI transition zone and set to 100% amplitude. The efficacy of decellularization was assessed using Harris hematoxylin and eosin, SYTOGreen nucleic acid and immunohistochemical stains for major histocompatibility complex I (MHC-I). Cell counts were performed manually using 5 random representative high power field (hpf, 20×) images of the TBI. Using the optimized protocol with high level ultrasonication, the ultimate tensile stress (UTS) of pair-matched grafts (Group 4, FIG. 6) was compared with control (Group 1, FIG. 3), using a materials testing system (Instron MTS 5955, as shown in FIG. 11).

Results.

Average cell counts per hpf were 105±47, 34±11, 15±11, 9±11 for Groups 1-4 respectively (p=0.00006, one-way ANOVA). Decellularization using a combination of physical and chemical treatments (Group 4, FIG. 6) resulted in substantial reduction of visible cells, nucleic material and MHC-1 complexes. There was no difference in UTS in treated (Group 4, FIG. 6) and untreated (Group 1, FIG. 3) samples (p=0.50, paired T-test).

Conclusions.

Figure 4:
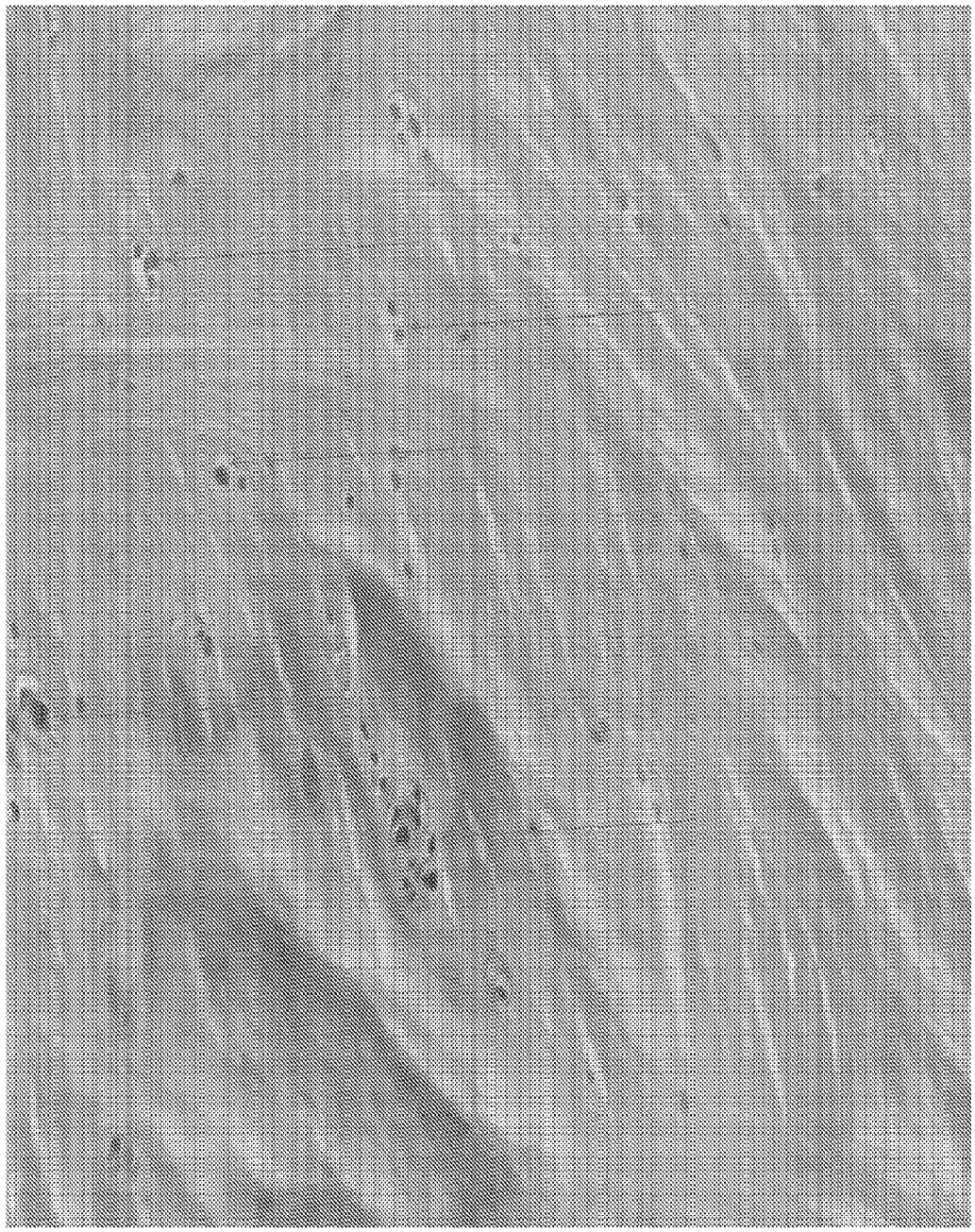
FIG. 4 shows the transition zone histology of TBI constructs ("Group 2") that were treated with chemical oxidants alone. There is marked depletion of cellular material, but scattered cells (see arrows) are still found in the cartilaginous zones.
Figure 5:
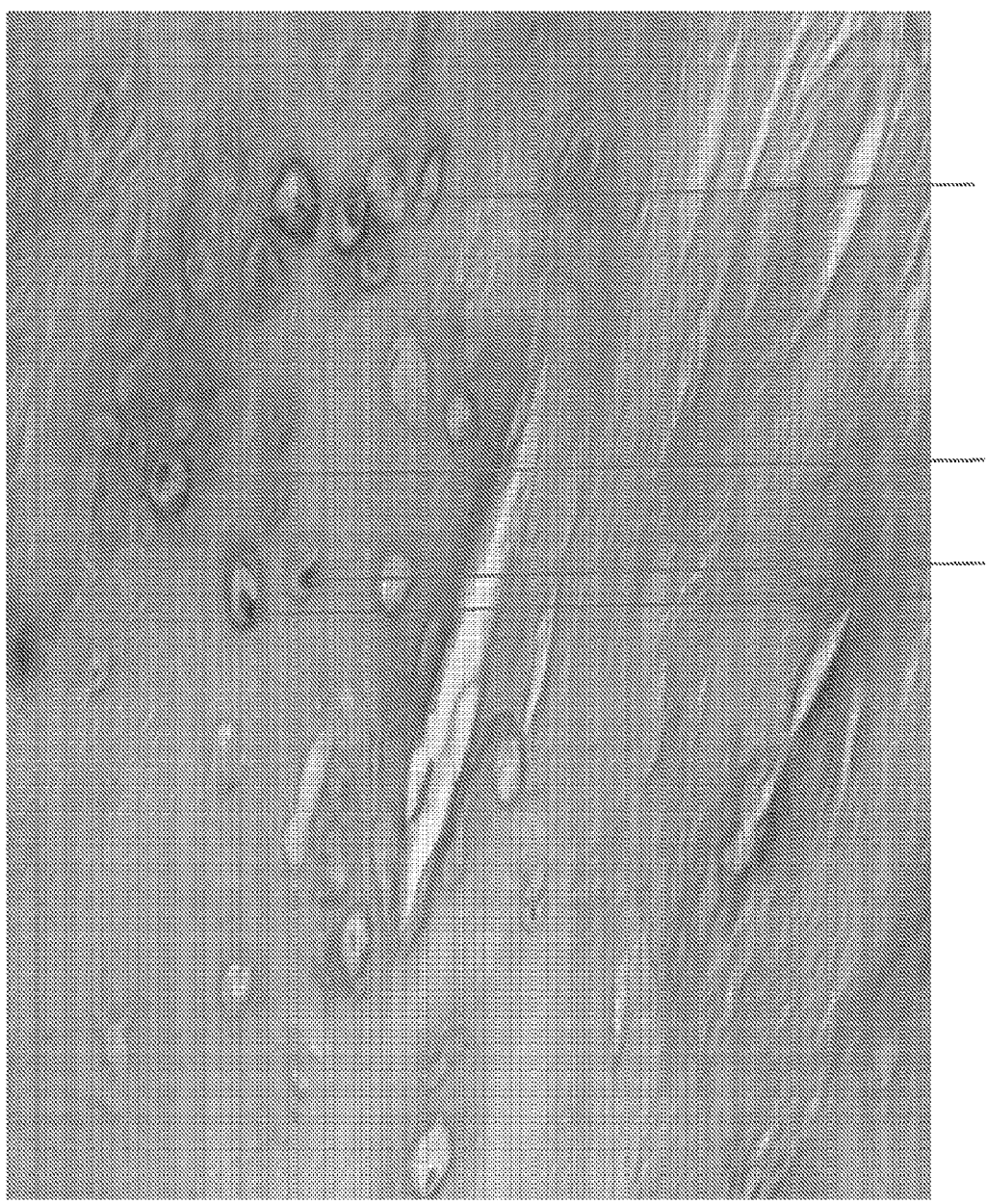
FIG. 5 shows the transition zone histology of TBI constructs ("Group 3"), that were decellularized using a low level of ultrasonication energy in addition to detergents and chemical oxidants. There is near-complete depletion of cellular material (remaining cells are marked with arrows), in comparison to FIGS. 3 and 4.

Physicochemical treatment of the TBI transition zone using a combination of high power ultrasonication and chemical agents resulted in near-complete depletion of cellularity (Group 4, FIG. 6) and superior decellularization compared with chemical methods alone (Group 2, EDTA-SDS, FIG. 4). There was also considerable improvement over physicochemical decellularization using low power ultrasonication and chemical agents (Group 3, FIG. 5).

Treatment of TBI composite constructs with targeted ultrasonication at the transition zone, porositization, and detergent treatment produced host-compatible composite tissue grafts suitable for use in surgical reconstruction of the tendon-bone and ligament-bone interface in humans and animals.

Example 2: Physicochemical Decellularization of Human Bone-Ligament-Bone Composite (BLBC) Grafts for Dorsal Scapholunate Ligament (DSLL) Reconstruction The scapholunate interosseus ligament (SLIL) is considered the primary stabilizer of the wrist. Chronic scapholunate (SL) dissociation results in dorsal intercalated segmental instability (DISI) and late scapholunate advanced collapse (SLAC) pattern of wrist arthritis.

Tenodesis procedures for chronic SL dissociation reconstruct only the DSLL because it is the strongest and contributes the most to stability and pre-injury wrist kinematics. Tendon-based DSLL reconstruction tends to stretch out over time because of the differing elastic properties of tendons and ligaments.

In contrast, bone-ligament-bone composite (BLBC) autografts are attractive because they attempt replacement of "like with like".

Tissue Harvest.

Proximal (P1) and middle (P2) phalanges with attached collateral ligaments were harvested from human cadaver forearms (Science Care, Phoenix, Ariz.). The constructs were then stored in PBS at −70° C. until further use. Then the circumferential skin and soft tissue, extensor hood and insertion, sagittal and lateral bands, radial and ulnar neurovascular bundles, and flexor digitorum superficialis (FDS) insertion were removed.

Mechanical Preparation.

The constructs were thawed to room temperature and then further prepared by transection of the phalangeal bone across the metaphysis and careful, thorough removal of the articular cartilage (P2 base, P1 head).

Methods.

Figure 7:
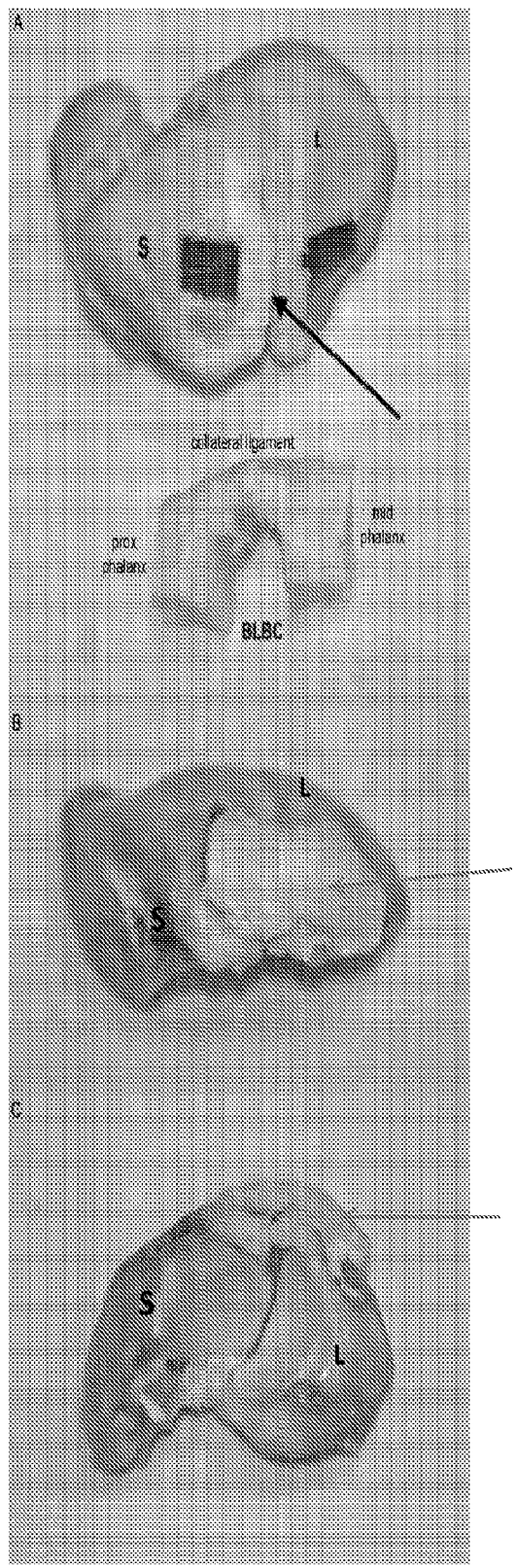
FIG. 7a shows the creation of a bone-ligament-bone composite (BLBC) graft based on the collateral ligament of the proximal interphalangeal joint of an upper limb digit (the BLBC is proximal phalanx—collateral ligament—middle phalanx). Bone plugs at either end are fashioned from the proximal phalanx head and middle phalanx base, respectively. The composite BLBC graft is used for reconstruction of dorsal scapholunate ligament (DSLL) tears. "S" shows the scaphoid side and "L" the lunate side.
FIGS. 7b and 7c show the BLBC graft inset (marked with arrows) into similar bone troughs in the scaphoid and lunate.

Using fresh-frozen cadaveric upper limbs, the index, middle and ring fingers proximal interphalangeal joints (PIPJ) were transected with adjacent (proximal and middle) phalanges (FIG. 7). All soft tissues including volar plates, extensor apparatus, skin, tendons, were removed leaving only the proper collateral ligament bone-ligament-bone complex (BLBC) on one (radial or ulnar) side.

Decellularization.

Using a matched-pair design, one isolated PIPJ collateral ligament of each pair was decellularized according to the protocol described above in Example 1.

Graft Fabrication.

Figure 8:
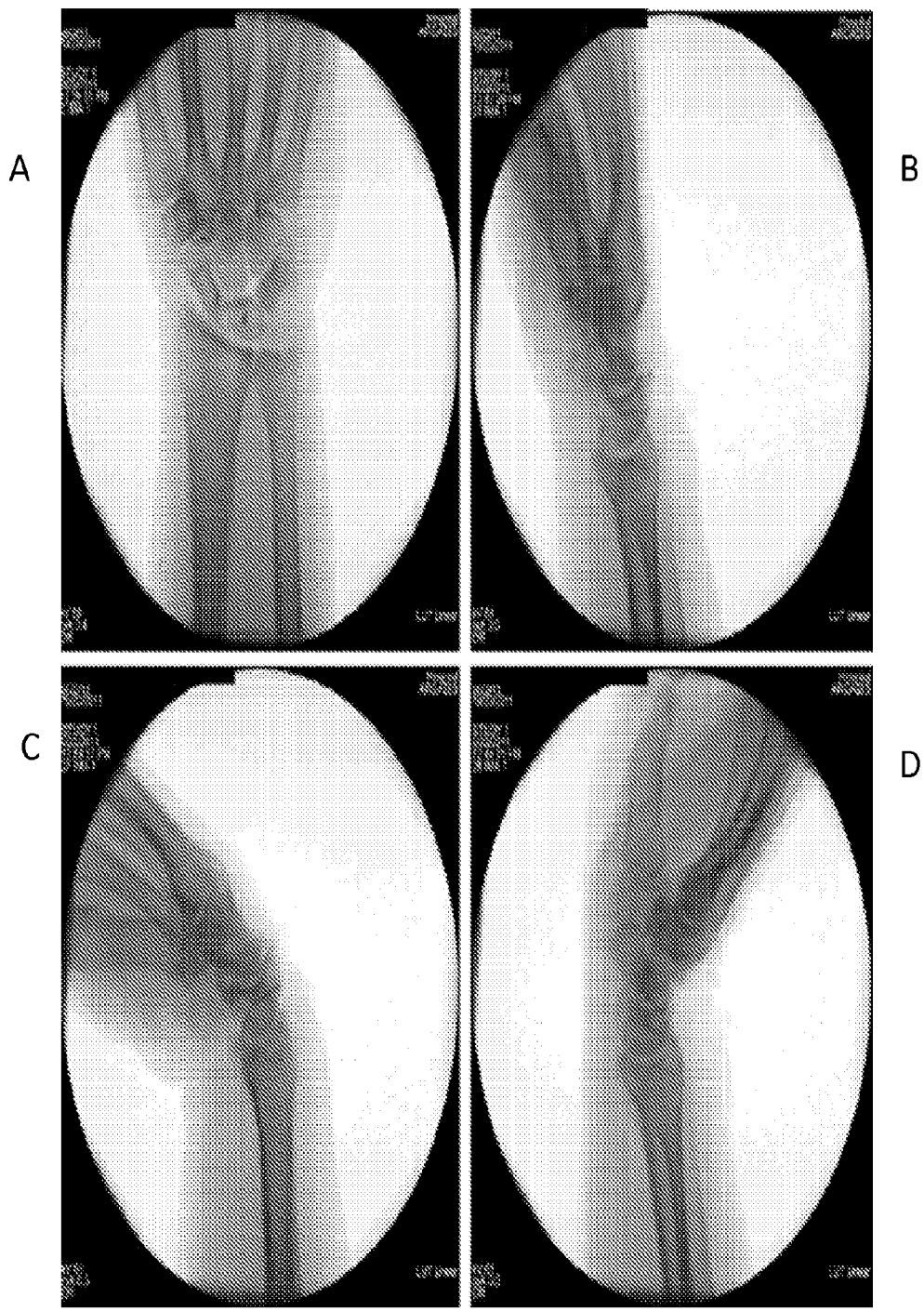
FIG. 8 shows the bone-ligament-bone composite inset and fixed grafts in positions of flexion (B, C, D) and extension (A). There is no graft impingement at extremes of flexion or extension.

Bone plugs were resected from the proximal phalanx (P1) head and middle phalanx (P2) base using the microsagittal saw (Stryker) and lifted en bloc with the isolated PIPJ collateral ligament (FIG. 8). Joint articular cartilage was resected.

Trough Fabrication.

The BLBC grafts were anchored to the dorsal lip of the scaphoid and lunate, overhanging the capitate fossa. The location of the lunate trough corresponds to the attachment of the dorsal intercarpal ligament (DIC). The scaphoid trough is located horizontally across from the lunate trough. Bone troughs measuring 4-8 mm (transverse)×4 mm (longitudinal)×4 mm (deep) were cut with an oscillating microsagittal saw and burr (Stryker, Kalamazoo, Mich.).

Graft Inset.

Figure 9:
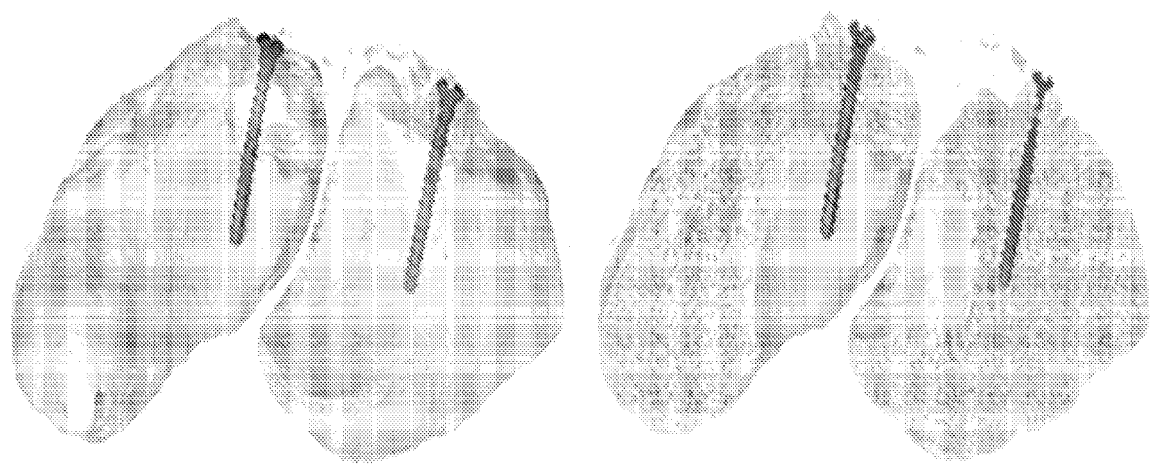
FIG. 9 depicts a micro-computed tomography image of the bone-ligament-bone composite graft inset into the scaphoid and lunate bones and fixed with screws (left, surface plane; right, cut plane).

BLBC grafts were then inset into the carpal troughs and thread holes were drilled (1.0 mm, Stryker). Bone plugs were fixed with 1.2 mm×10 mm self-tapping cortical screws (Stryker). Following hardware fixation, wrists were ranged through flexion and extension visually and under fluoroscopic control (FIG. 8) to detect screw thread penetration of the scaphocapitate joint and radiocarpal impingement. Detailed postoperative imaging with computed tomography may be performed for closer visualization (FIG. 9).

Biomechanical Testing.

Collateral and SLIL ligaments dimensions were recorded with a digital caliper. Bone ends of DSLL, BLBC, isolated allograft PIPJ collateral ligaments and SL repairs with BLBC grafts were potted in methylmethacrylate, isolating the ligamentous portion and its bony insertion for mechanical testing. With SL repairs with BLBC grafts, BLBC grafts were inset and fixed with screws into scaphoid and lunate pairs and the respective carpal bones potted. Indices recorded include ultimate strength (N), stiffness (slope of force-displacement curve, N/mm), and site of failure (mid-ligamentous, ligament insertion, or bony fracture). We compared ultimate strength and stiffness for (1) native DSLL, (2) untreated isolated PIPJ collateral ligaments (attached to phalanges), (3) decellularized isolated PIPJ collateral ligaments (attached to phalanges) and (4) SL repairs with BLBC grafts.

Histologic Analysis.

Untreated and decellularized BLBC specimens were fixed in 10% formalin and decalcified overnight. Specimens were embedded in paraffin, sectioned (8 μm) and stained with Harris hematoxylin and eosin to determine the adequacy of decellularization and preservation of collagenous architecture.

Lentivirus Production.

In order to positively identify in vitro reseeded cells, candidate seed cells were labeled with green fluorescent protein (GFP) using a lentiviral vector. pUbi-luc2-eGFP plasmids were constructed in a manner previously described (Patel, 2010). High-titer lentiviral vectors were produced using a modified version of the protocol described by Zhang et al (Zhang, 2007).

Creation of GFP Positive Mesenchymal Stem Cell Line

Commercially obtained adipoderived stem cells (ADSCs) (Poietics PT-5006 cryopreserved adipoderived stem cells, Lonza, Walkersville, Md.) were cultured in ADSC basal medium (ADSC-BM, Lonza) augmented with 10% FCS (Gibco). The cells were transduced with lentivirus carrying an ubiquitin promoter driving a bifusion reporter of firefly luciferase reporter gene (luc2) and an enhanced green fluorescent protein (eGFP) gene at a multiplicity of infection of 50. The genetically modified ADSC (ADSC-pUbi-luc2-eGFP) underwent two rounds of FACS sorting (FACSAria III, Becton Dickinson, San Jose, Calif.) and were used for both cell culture and graft reseeding experiments.

Reseeding.

As a proof of concept, grafts were reseeded for 6 hours in hermetically sealed tubes using a cell suspension comprising $1-2 \times 10^6$ ADSC/ml at 37° C. on a rotator. Following reseeding, constructs were transferred into sterile polypropylene tubes with stem cell media for 5 days. At the end of the 5-day consolidation period, constructs were fixed in paraformaldehyde, decalcified in 19% EDTA, embedded in OCT and sectioned with a cryostat (8 μm). Sections were mounted on slides and observed using an inverted microscope.

Results from Biomechanical Testing to Evaluate the Suitability of the Bioscaffold for Grafting.

Ultimate Strength. There was no difference in ultimate strength between native DSLL, untreated PIPJ ligaments, decellularized ligaments and SL repairs with BLBC grafts (p=0.12, one-way ANOVA). Similarly, no difference was observed in ultimate strength of pair-matched (n=11 pairs) native and decellularized collateral ligaments pairs (p=0.44, paired T-test). Among digits, no difference was detected in ultimate strength between index (181.6±51.6N), middle (176.2±36.1N) and ring fingers (176.7±37.2N) PIPJ collateral ligaments (p=0.62, one-way ANOVA). Among pooled radial- and ulnar-sided ligaments, no difference was found in ultimate strength between the radial collateral ligament (RCL) (170.4±42.7N) and the ulnar collateral ligament (UCL) (187.4±38.1, p=0.24, T-test) of the metacarpophalangeal joint of the thumb.

Stiffness.

There was no difference in stiffness between native DSLL, untreated PIPJ ligaments, decellularized ligaments and SL repairs with BLBC grafts (p=0.85, one-way ANOVA). There was no difference in stiffness between pair-matched untreated and decellularized ligament pairs (p=0.07, paired T-test). Among digits, there was no difference in stiffness between index (55.6±18.3N), middle (55.5±11.8N) and ring finger (50.2±15.5N) ligaments (p=0.64, one-way ANOVA).

Displacement to Failure.

There was no difference in displacement to failure between native DSLL, untreated collateral ligaments, decellularized collateral ligaments and SL repairs with BLBC grafts (p=0.11, one-way ANOVA). However, evaluation of pair-matched ligaments revealed greater displacement to failure in untreated ligaments (5.75±0.99 mm) compared with decellularized ligaments (4.30±1.08 mm, p=0.005) but the latter was not significantly different from the native DSLL tested (p=0.69).

Histology.

Figure 10:
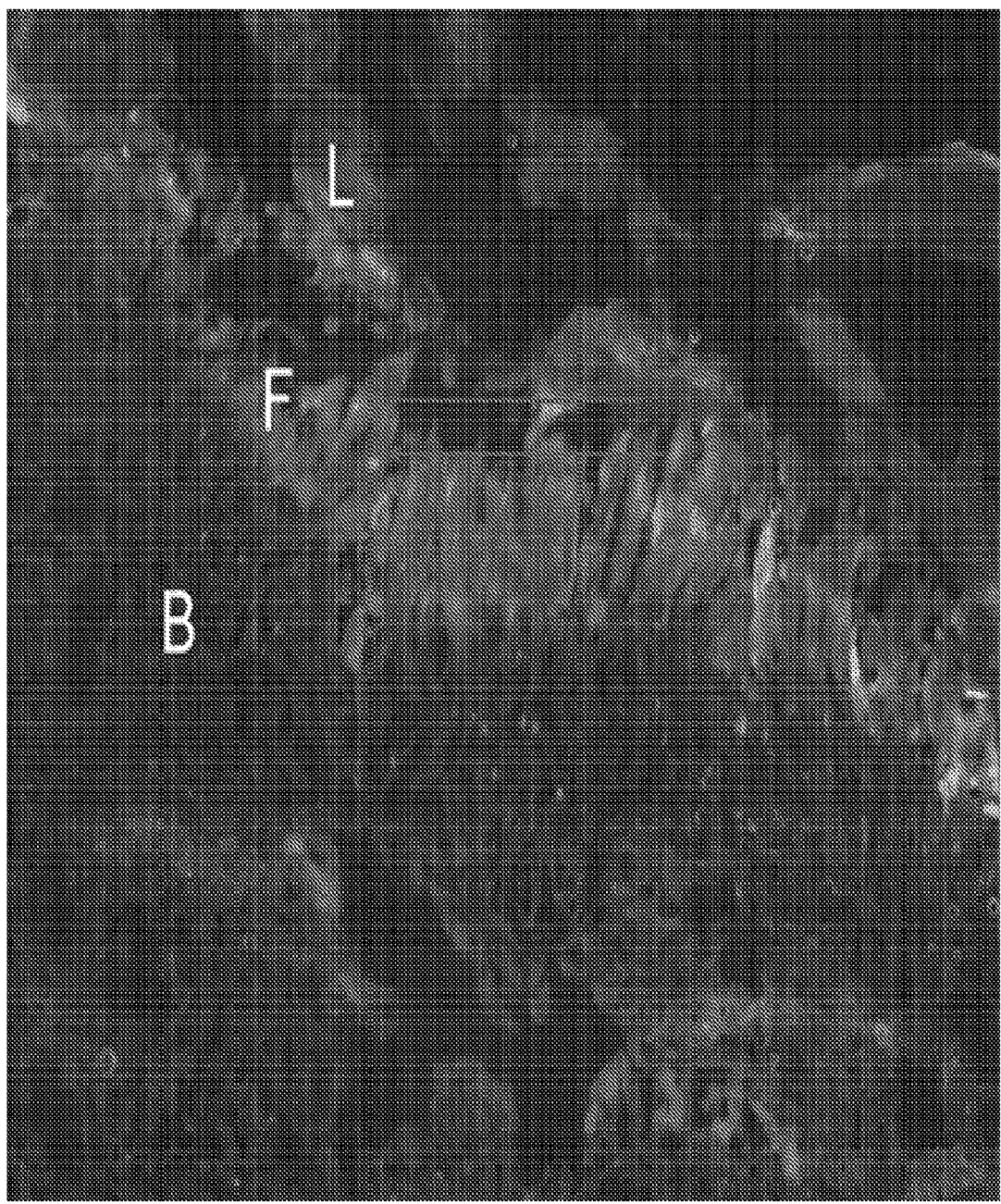
FIG. 10 shows frozen section images depicting ex vivo re-seeding of bone-ligament-bone composite (BLBC) grafts with mesenchymal stem cells cells expressing green fluorescent protein (GFP). These cells have been transfected with a virus bearing a plasmid encoding GFP. Bright green dots represent seeded cells (see arrows). The transition zone (ligament-bone interface) is depicted (L, ligament; F, fibrocartilage; B, bone).

Histologic analysis revealed successful decellularization of the entire BLBC. There was reestablishment of cellularity following reseeding with GFP-labeled cells (FIG. 10).

Conclusions.

BLBC grafts fashioned from the PIPJ collateral ligaments of index, middle, and ring fingers proved viable substitutes for the native SL ligament in DSLL reconstruction. Using a graft with similar dimensions to the native DSLL further allows for anatomical reconstruction with little fear of radiocarpal impingement upon wrist dorsiflexion (FIG. 8). The Decellularization procedure used was found to not adversely affect scaffold integrity, strength or stiffness. The BLBC scaffolds were successfully reseeded with mesenchymal stem cells as a proof-of-concept (FIG. 10). Reseeded single-tissue and composite tissue grafts may hold the key to "jump starting" of the remodeling process.

As demonstrated, the grafts could be fixed in carpal troughs to recreate the ruptured DSLL, and that the material properties (strength, stiffness, displacement to failure) of these constructs were found comparable to that of native DSLL. However, closer analysis of pair-matched constructs revealed a slight increase in stiffness following decellularization. It is not known if increased stiffness in the absence of a change in strength will have a significant adverse clinical effect on these grafts in vivo.

It was further demonstrated that BLBC grafts did not display inferior biomechanical properties following trimming and implantation. Grafts are often dissected down to size prior to inset, leading to loss of graft width and total fiber number, and reduction in the size of the bony footprint, leading to reduced trough interference fit. Thus, testing of untrimmed ligaments might overestimate their biomechanical properties compared to that of trimmed, inset grafts. The biomechanical testing model is considered to closely reproduce the actual post-operative strength of these grafts following clinical implantation.

Bone-to-bone healing is believed to lead to a more robust construct than direct suture repair of remnant SL ligaments or reattachment of torn ligament to bone.

Potential off-the-shelf allografts, such as the proposed PIPJ collateral ligament grafts have the advantages of reduced operative time for autograft harvest and avoidance of donor site morbidity associated with sacrifice of other lower or upper extremity ligaments. In addition, a single cadaveric upper limb source will yield multiple, easily harvested grafts, making these grafts attractive for future upscaled processing.

Example 3: Orthotopic Reimplantation of Decellularized Phalanx-Flexor Tendon Composite Grafts for Extensive Composite Tissue Loss The human FDP tendon-distal phalanx complex is the primary flexor of the distal interphalangeal joint (DIPJ). This complex also flexes the proximal interphalangeal joint (PIPJ) and metacarpophalangeal joint (MCPJ) secondarily. The FDP tendon-distal phalanx complex is also indirectly responsible for extension of the interphalangeal joints through the indirect action of digital lumbrical muscles, which take origin from the FDP tendon, and insert on the lateral bands.

Complex tendon-bone losses involve
a. long segments of flexor tendon—where single or multiple tendons are lost, leading to exhaustion of available autogenous graft;
b. composite tissue loss—where tendon and its bony attachment are lost; or
c. insertional loss—where the tendon-bone interface is destroyed.

Complex tendon-bone losses are traditionally addressed by direct distal tendon graft-to-bone apposition and proximal tendon graft-to-residual tendon Pulvertaft weave. Tendon grafts used in these procedures include autogenous palmaris longus and plantaris tendons. Complex tendon-bone losses addressed in this fashion heal incompletely with scar tissue at the tendon-bone-attachment, leading to inferior tensile strength.

Orthotopic implantation of composite tendon-bone allografts, in contrast, is attractive because of the concept of replacing "like with like". Prior to implantation, it is necessary to decellularize allograft tissue to neutralize immunogenicity and reduce risk of disease transmission.

Methods.

Graft harvest. FDP tendons with a piece of distal phalanx (DPFT; distal phalanx-flexor tendon constructs) were harvested en bloc from human cadaveric forearms. Proximally, tendons were transected 3 cm distal to the musculotendinous junction. Decellularization. Using a pair-matched design, DPFT constructs were divided into two groups: decellularized group and control group. The decellularized group was decellularized based on the technique discussed above. Orthotopic Implantation. Both test groups were then replaced into same defects in the same limbs from which they were harvested. A tie over button was used to secure the bone block into the distal phalanx while a Pulvertaft tendon weave was performed proximally between the FDP and a flexor digitorum superficialis tendon. Mechanical Cyclic Loading. Using a materials testing system (MTS), coaxial cyclic load was applied to the tip of each digit, creating full digital extension. The extended digit was then brought from full extension into full flexion by applying coaxial cyclic load in the opposite direction, at the proximal end of the tendon weave Each digit was cycled 50 times to ensure restoration of physiologic gliding characteristics, and to uncrimp collagen fibers. Biomechanical Testing. On completion, each construct was pulled to failure, and failure load and failure site were recorded.

Results.

There was no significant difference in strength between the decellularized and control groups (67.8 N and 78.1 N, respectively, p=0.3). Additionally, the points of failure were distributed similarly between the groups. Importantly, the tendon grafts withstood forces and displacement exceeding that of normal post-operative therapy regimens. This experiment demonstrated the suitability of composite tendon grafts for TBI reconstruction clinically in extremity reconstruction.

Conclusions.

DPFT composite allografts can be used to reconstruct complex flexor tendon losses involving long flexor tendon segments, and attached bone.

Example 4: Decellularized Tendon-Bone Composite Allografts Demonstrate Less Immune Reaction and Greater Biomechanical Strength in a Rat Model Allograft tissue transplantation is complicated if a host immune response is evoked in response to grafting of not-self, i.e. foreign, tissue. The immune response is directed at foreign cells and antigens, and ultimately results in the breakdown of foreign tissue.

In the case of orthotopic organ allotransplantation, intact organ cellularity is essential for optimal organ function. As such, immunosuppressive drugs are used to weaken the immune response and to prevent the rejection of transplanted tissues and organs. Since the immunosuppressive agents broadly affect the immune system, their administration leads eventually to a weakened immune system carrying the risk of opportunistic infections and neoplastic diseases.

In case of musculoskeletal allograft transplantations, the retention of the biomechanical properties of these tissues is much more important that the preservation of their cellularity. Biomechanical properties are characteristic of the tissue matrix and independent of cell survival following transplantation. Decellularization is a preferable approach to musculoskeletal tissue transplantations, since it results in reduced residual cellularity and a reduction in foreign antigens, which maintains the biomechanical properties of transplanted tissue.

Methods.

Graft Harvest. Composite Achilles tendon-calcaneus grafts were harvested from Wistar rats and divided into 2 groups. Grafts in Group 1 were decellularized using EDTA, SDS, peracetic acid and targeted ultrasonication of the tendon-bone insertion (TBI) as described in the Experimental Procedures. Grafts in Group 2 were untreated controls. Sprague-Dawley (SD) rats underwent Wistar TBI allograft reconstruction of bilateral hindlimb achilles tendon-calcaneus bone tendon-bone insertion sites using a pair-matched design (left, decellularized; right, untreated). SD rats were sacrificed at 2 or 4 weeks and the reconstructed hindlimbs were harvested. The extent of B-cells and macrophage infiltration was determined using immunohistochemistry (IHC). The explants were subjected to mechanical testing to determine the ultimate failure load. Statistical analysis was performed using a paired Student's T-test.

Results.

Figure 13:
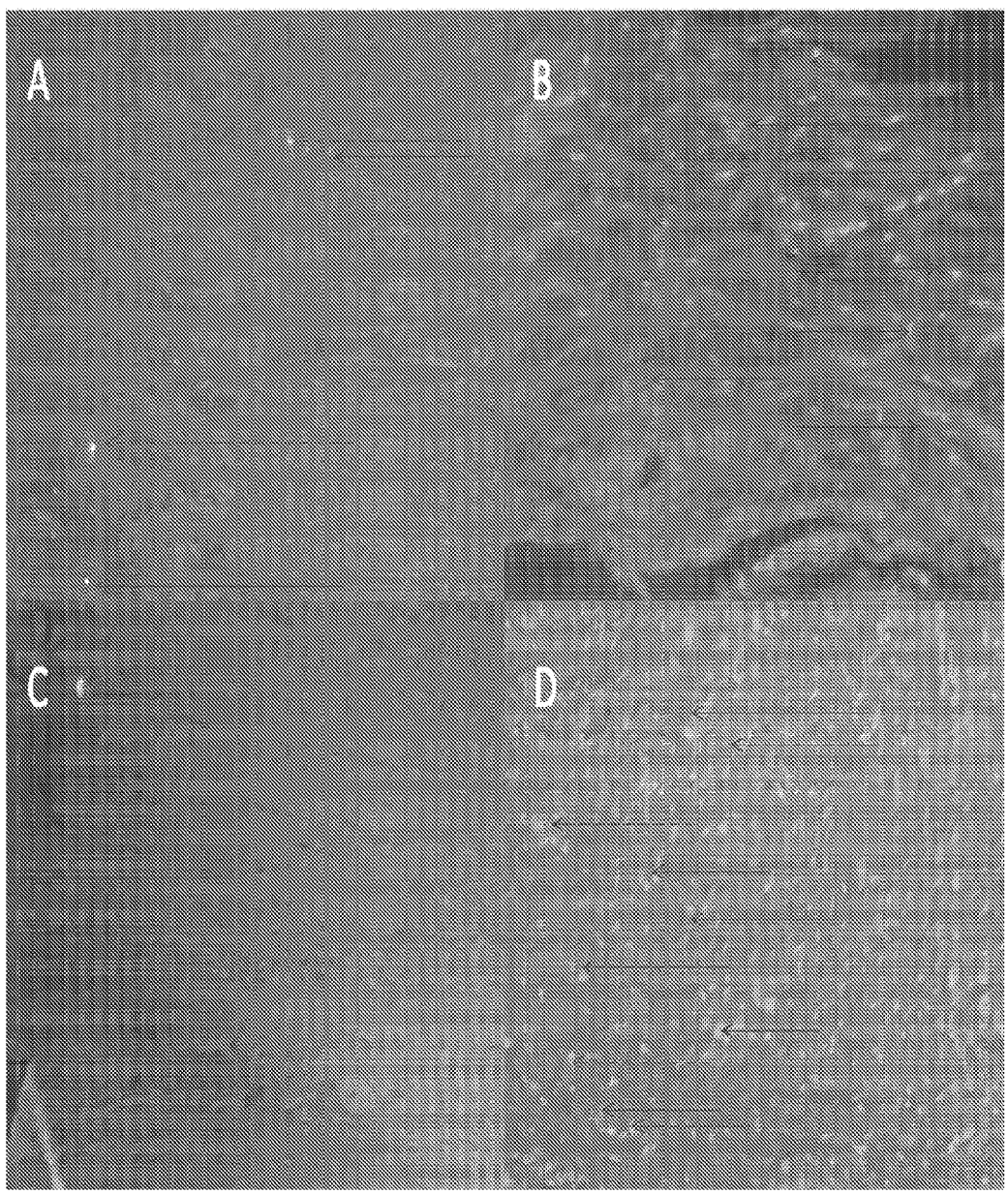
FIG. 13 illustrates IHC staining (20×) of CD20 positive lymphocytes (IHC) in the tendinous part of decellularized graft (A) and untreated graft (B) at 2 weeks (top) as well as in decellularized graft (C) and untreated graft (D) at 4 weeks (bottom) following reconstruction using a tendon-bone interface graft that was prepared with high level of ultrasonication. As clearly distinguishable to the untreated grafts B and D (arrows showing cells), the decellularized grafts A and C were almost free of cells (arrows showing cells).
Figure 14:
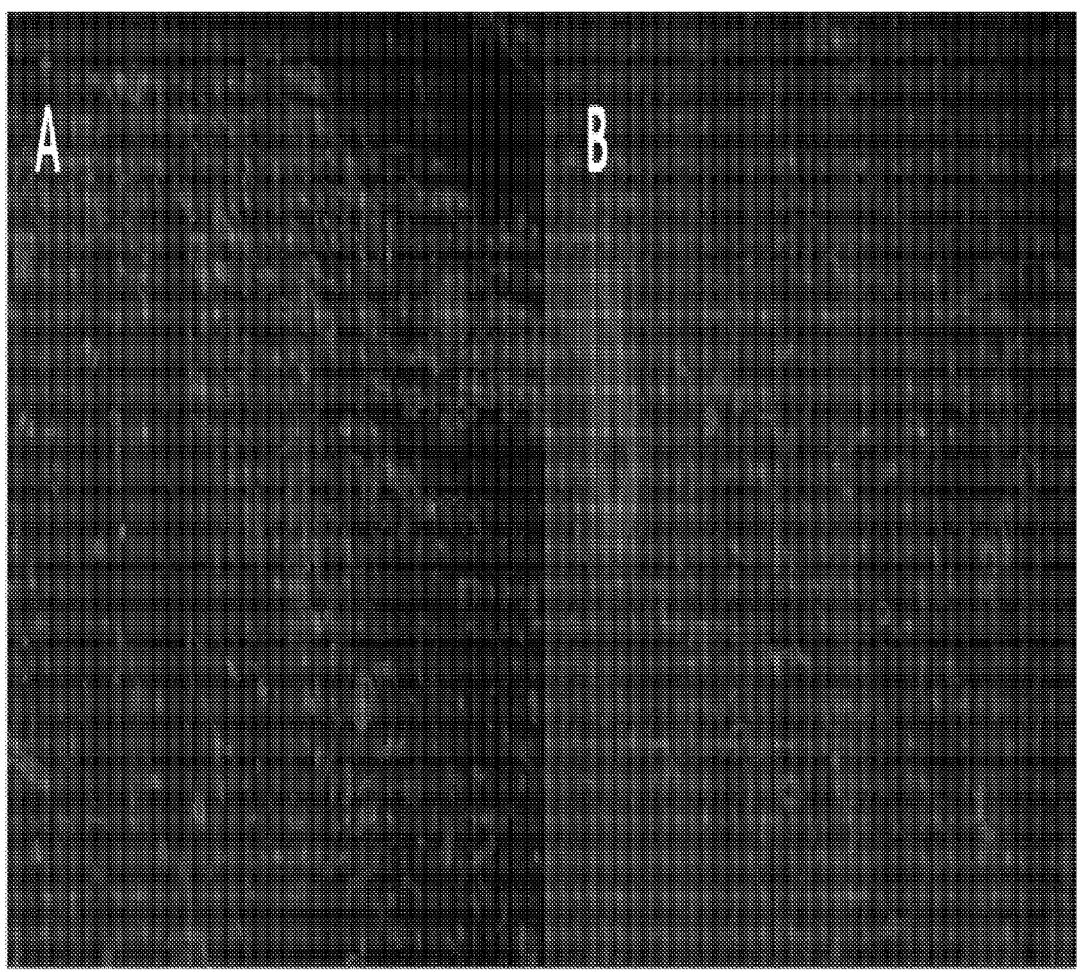
FIG. 14 illustrates IHC (20×) staining of CD20 positive lymphocytes at 4 weeks following reconstruction, showing an increased number of inflammatory cells in the capsule surrounding the tendon-bone interface in the untreated group (A) compared to the decellularized group (B).
Figure 15:
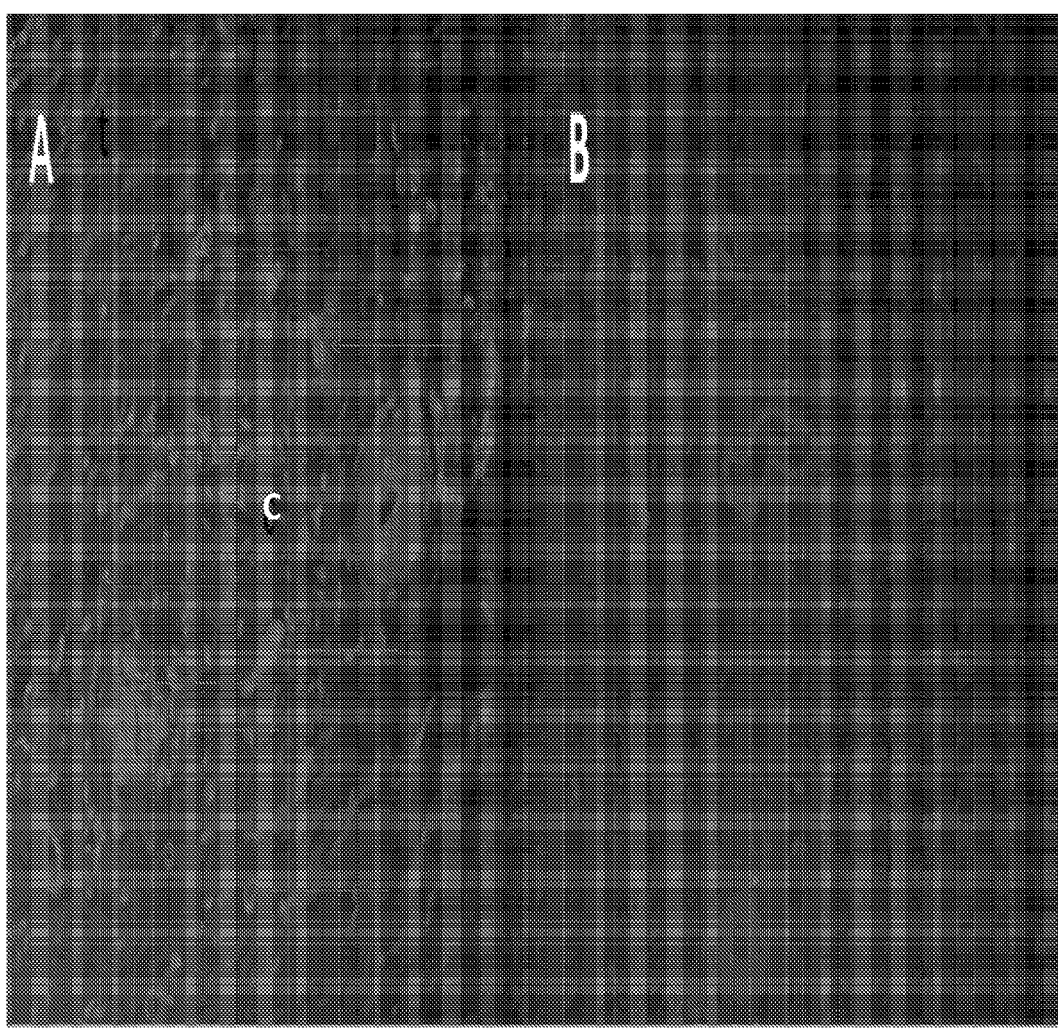
FIG. 15 illustrates IHC staining (20×) of CD68 positive macrophages at 4 weeks following reconstruction, showing an increased number of inflammatory cells (see arrows) in the capsule (c) as well as at the tendon (t) surrounding the tendon-bone interface in the untreated group (A) compared to the decellularized group (B).
Figure 16:
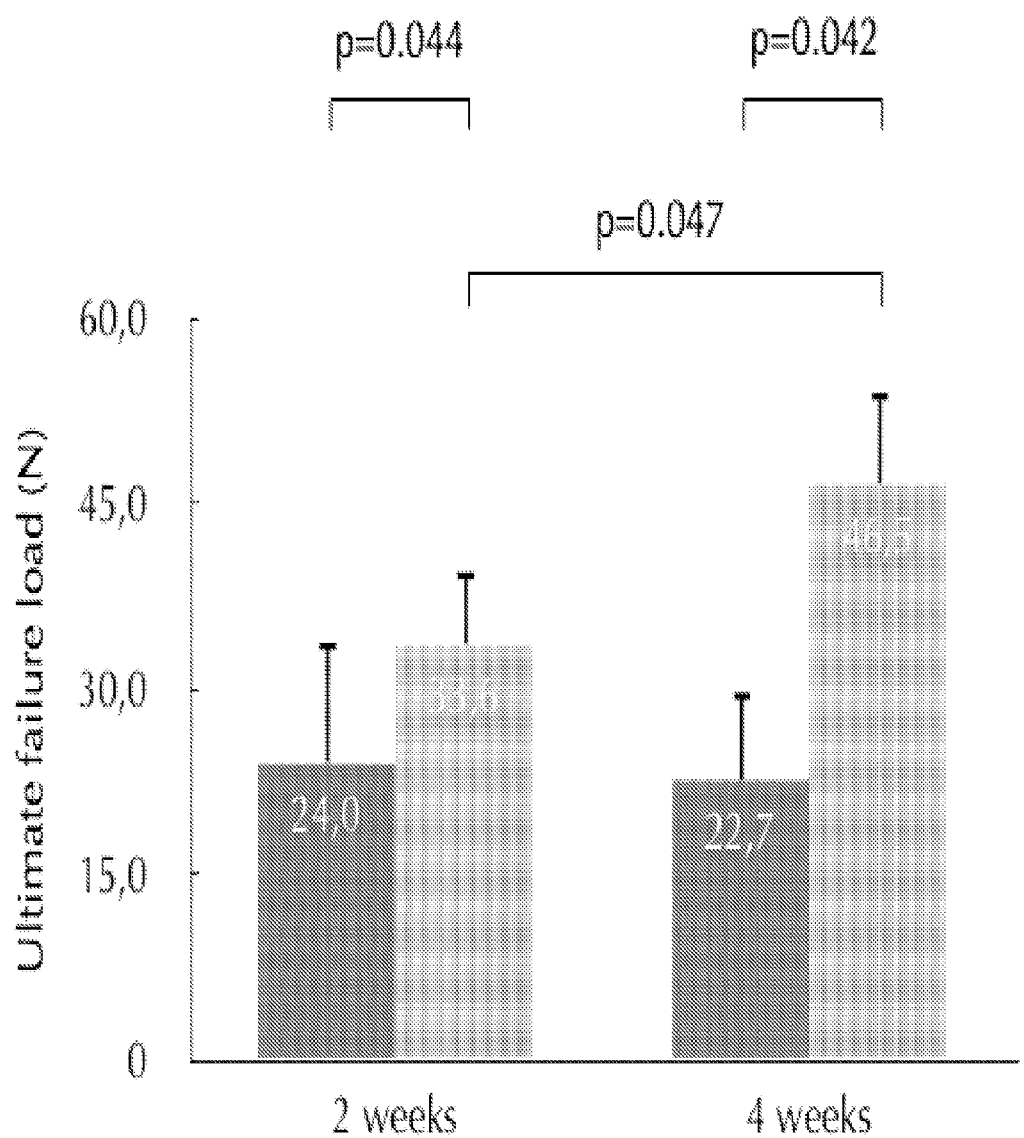
FIG. 16 illustrates results for the ultimate failure load test in human cadaver tendons for the untreated groups (dark blue) and decellularized groups (light blue) after 2 and 4 weeks, respectively.

In rats, that had been sacrificed two weeks following the reconstruction, there was increased B-cell and macrophage infiltration in Group 2 (untreated) compared with Group 1 (decellularized), both in the capsule surrounding the TBI and the tendon substance. There was improved ultimate failure load (33.6±7.5N vs 24.0±9.8N, respectively, p=0.044) in Group 1 (decellularized), see FIG. 16. At 4 weeks, there was persistent B-cell and macrophage infiltration in Group 2 (untreated) compared with Group 1 (decellularized), see FIGS. 13, 14 and 15. At 4 weeks, Group 1 (decellularized) demonstrated persistently greater ultimate failure load (46.5±7.5N vs 22.7±7.3N, respectively, p=0.042) compared with Group 2 (untreated), see FIG. 16. Conclusions: Targeted physicochemical decellularization of tendon-bone composite grafts removes cell surface antigens leading to a decreased immune response when used for allograft reconstruction. These grafts showed better biomechanical properties at 2 and 4 weeks when compared with control (untreated) tendons. Decellularization is an important step in the processing of tissue engineered tendon-bone composite grafts for upper extremity TBI reconstruction.

Although the foregoing invention and its embodiments have been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. Accordingly, the preceding merely illustrates the principles of the invention. It will be appreciated that those skilled in the art will be able to devise various arrangements which, although not explicitly described or shown herein, embody the principles of the invention and are included within its spirit and scope.

REFERENCES

Amadio, P. C., Wood, M. B., Cooney, W. P. & Bogard, S. D. Staged flexor tendon reconstruction in the fingers and hand. *J Hand Surg Am* 13, 559-562 (1988).

Awad, H. A. et al. Repair of patellar tendon injuries using a cell-collagen composite. *J. Orthop. Res* 21, 420-431 (2003).

Bagnaninchi, P. O. et al. Chitosan microchannel scaffolds for tendon tissue engineering characterized using optical coherence tomography. *Tissue Eng* 13, 323-331 (2007).

Bagnaninchi P O, Yang Y, El Haj A J, Maffulli N. Tissue engineering for tendon repair. *British journal of sports medicine.* 2007b; 41:e10; discussion e10.

Boyer, M. I., Strickland, J. W., Engles, D., Sachar, K. & Leversedge, F. J. Flexor tendon repair and rehabilitation: state of the art in 2002. *J Bone Joint Surg Am* 84, 1684-1706 (2002).

Cao, Y. et al. Bridging tendon defects using autologous tenocyte engineered tendon in a hen model. *Plast. Reconstr. Surg* 110, 1280-1289 (2002).

Chan, B. P. & Leong, K. W. Scaffolding in tissue engineering: general approaches and tissue-specific considerations. *Eur Spine J* 17 Suppl 4, 467-479 (2008).

Chong A K, Chang J. Tissue engineering for the hand surgeon: a clinical perspective. *J Hand Surg Am.* 2006; 31:349-358

Cooper, J. A., Lu, H. H., Ko, F. K., Freeman, J. W. & Laurencin, C. T. Fiber-based tissue-engineered scaffold for ligament replacement: design considerations and in vitro evaluation. *Biomaterials* 26, 1523-1532 (2005).

DeFranco, M. J., Derwin, K. & Iannotti, J. P. New therapies in tendon reconstruction. *J Am Acad Orthop Surg* 12, 298-304 (2004)

Farrington M, Wreghitt T, Matthews I, et al. Processing of cardiac valve allografts: 2. Effects of antimicrobial treatment on sterility, structure and mechanical properties. *Cell Tissue Bank.* 2002; 3:91-103.

Gelberman, R. H., Seiler, J. G., Rosenberg, A. E., Heyman, P. & Amiel, D. Intercalary flexor tendon grafts. A morphological study of intrasynovial and extrasynovial donor tendons. *Scand J Plast Reconstr Surg Hand Surg* 26, 257-264 (1992a).

Gelberman, R. H., Chu, C. R., Williams, C. S., Seiler, J. G. & Amiel, D. Angiogenesis in healing autogenous flexor-tendon grafts. *J Bone Joint Surg Am* 74, 1207-1216 (1992b).

Gilbert, T. W., Sellaro, T. L. & Badylak, S. F. Decellularization of tissues and organs. *Biomaterials* 27, 3675-3683 (2006).

Hudson, T. W. et al. Optimized acellular nerve graft is immunologically tolerated and supports regeneration. *Tissue Eng* 10, 1641-1651 (2004).

Ingram J H et al. (2007). The use of ultrasonication to aid recellularization of acellular natural tissue scaffolds for use in anterior cruciate ligament reconstruction. *Tissue Eng* 13:1561-72.

Kannus, P. Structure of the tendon connective tissue. *Scand J Med Sci Sports* 10, 312-320 (2000).

Kasimir, M. T. et al. Comparison of different decellularization procedures of porcine heart valves. *Int J Artif Organs* 26, 421-427 (2003).

Kim, B., Yoo, J. J. & Atala, A. Peripheral nerve regeneration using acellular nerve grafts. *J Biomed Mater Res A* 68, 201-209 (2004).

Khan U, Occleston N L, Khaw P T, McGrouther D A. Differences in proliferative rate and collagen lattice contraction between endotenon and synovial fibroblasts. *J Hand Surg Am.* 1998; 23:266-273.

Klein M B, Pham H, Yalamanchi N, Chang J. Flexor tendon wound healing in vitro: the effect of lactate on tendon cell proliferation and collagen production. *J Hand Surg Am.* 2001; 26:847-854.

Kryger G S, Chong A K, Costa M, Pham H, Bates S J, Chang J. A comparison of tenocytes and mesenchymal stem cells for use in flexor tendon tissue engineering. *J Hand Surg Am.* 2007; 32:597-605.

Leversedge, F. J., Zelouf, D., Williams, C., Gelberman, R. H. & Seiler, J. G. Flexor tendon grafting to the hand: an assessment of the intrasynovial donor tendon-A preliminary single-cohort study. *J Hand Surg Am* 25, 721-730 (2000).

Liu, W. et al. Repair of tendon defect with dermal fibroblast engineered tendon in a porcine model. *Tissue Eng* 12, 775-788 (2006).

Liu, Y., Ramanath, H. S. & Wang, D. Tendon tissue engineering using scaffold enhancing strategies. *Trends Biotechnol* 26, 201-209 (2008).

Lomas R J, Cruse-Sawyer J E, Simpson C, Ingham E, Bojar R, Kearney J N. Assessment of the biological properties of human split skin allografts disinfected with peracetic acid and preserved in glycerol. *Burns* 2003; 29:515-525.

Lomas R J, Jennings L M, Fisher J, Kearney J N. Effects of a peracetic acid disinfection protocol on the biocompatibility and biomechanical properties of human patellar tendon allografts. *Cell. Tissue Bank.* 2004; 5:149-160.

Lundborg, G. Experimental flexor tendon healing without adhesion formation—a new concept of tendon nutrition and intrinsic healing mechanisms. A preliminary report. *Hand* 8, 235-238 (1976).

Merguerian, P. A. et al. Acellular bladder matrix allografts in the regeneration of functional bladders: evaluation of large-segment (>24 cm) substitution in a porcine model. *BJU Int* 85, 894-898 (2000).

Nishida, J., Amadio, P. C., Bettinger, P. C. & An, K. N. Flexor tendon-tendon sheath interaction after tendon grafting: a biomechanical study in a human model in vitro. *The Journal of hand surgery* 24, 1097-1102 (1999).

Ouyang, H. W., Goh, J. C. H., Thambyah, A., Teoh, S. H. & Lee, E. H. Knitted poly-lactide-co-glycolide scaffold loaded with bone marrow stromal cells in repair and regeneration of rabbit Achilles tendon. *Tissue Eng* 9, 431-439 (2003).

Patel, M. R., Chang, Y. F., Chen, I. Y., Bachmann, M. H., Yan, X., Contag, C. H., Gambhir, S. S. Longitudinal, noninvasive imaging of T-cell effector function and proliferation in living subjects. Cancer Res 70, 10141-10149 (2010).

Pruss A, Kao M, Kiesewetter H, von Versen R, Pauli G. Virus safety of avital bone tissue transplants: evaluation of sterilization steps of spongiosa cuboids using a peracetic acid-methanol mixture. *Biologicals.* 1999; 27:195-201.

Pulvertaft R G. Suture materials and tendon junctures. American Journal of Surgery, 109: 346-352 (1965).

Seiler, J. G., Chu, C. R., Amiel, D., Woo, S. L. & Gelberman, R. H. The Marshall R. Urist Young Investigator Award. Autogenous flexor tendon grafts. Biologic mechanisms for incorporation. *Clin. Orthop. Relat. Res* 239-247 (1997).

Sharma, P. & Maffulli, N. Tendon injury and tendinopathy: healing and repair. *J Bone Joint Surg Am* 87, 187-202 (2005).

Takami, Y., Matsuda, T., Yoshitake, M., Hanumadass, M. & Walter, R. J. Dispase/detergent treated dermal matrix as a dermal substitute. *Burns* 22, 182-190 (1996).

Thomopoulos S et al. (2010). The development and morphogenesis of the tendon-to-bone insertion—what development can teach us about healing. *J Musculoskelet Neuronal Interact* 10:35-45.

Uchiyama, S., Amadio, P. C., Coert, J. H., Berglund, L. J. & An, K. N. Gliding resistance of extrasynovial and intrasynovial tendons through the A2 pulley. *J Bone Joint Surg Am* 79, 219-224 (1997).

Ueda, Y. et al. Antigen clearing from porcine heart valves with preservation of structural integrity. *Int J Artif Organs* 29, 781-789 (2006).

White W L (1960). Tendon grafts: a consideration of their source, procurement and suitability. *Surg Clin North Am* 40:403-413.

Yao L, Bestwick C S, Bestwick L A, Maffulli N, Aspden R M. Phenotypic drift in human tenocyte culture. *Tissue Eng.* 2006; 12:1843-1849.

Zhang A Y & Chang J (2003). Tissue engineering of flexor tendons. *Clin Plast Surg* 30:565-572.

Zhang A Y et al. (2009). Tissue-engineered intrasynovial tendons: optimization of acellularization and seeding. *J Rehabil Res Dev* 46:489-498.

Zhang, F., Wang, L. P., Brauner, M., Liewald, J. F, Kay, K., Watzke, N., Wood, P. G., Bamberg, E., Nagel, G., Gottschalk, A., Deisseroth, K. Multimodal fast optical interrogation of neural circuitry. *Nature* 446, 633-639 (2007).

What is claimed is:

1. A method of producing a composite tissue bioscaffold for implantation into a mammalian graft recipient in need of surgical soft tissue-hard tissue interface reconstruction,
    said method comprising
    harvesting soft tissue, hard tissue and soft-hard tissue interface from a mammalian cadaver,
    subjecting said interface only to targeted ultrasonication, and
    contacting said soft tissue, hard tissue, and interface with detergents and chemical oxidants to remove extracellular matrix materials, wherein the targeted ultrasonication of said interface results in removal of at least 90% of cells from said interface while retaining the tissues' and tissue interface's native biomechanical integrity, thereby rendering the bioscaffold host-compatible and suitable for surgical tissue interface reconstruction.

2. The method according to claim 1, wherein said composite tissue was obtained from an allogeneic source.

3. The method according to claim 1, wherein said composite tissue was obtained from a xenogeneic source.

4. The method according to claim 1, wherein said bioscaffold comprises a tendon, bone, and tendon-bone interface.

5. The method according to claim 1, wherein said bioscaffold comprises a ligament, bone, and ligament-bone interface.

6. A composite tissue bioscaffold for implantation into a mammalian graft recipient in need of surgical soft tissue-hard tissue interface reconstruction, said bioscaffold comprising a soft tissue, a hard tissue and a soft-hard tissue interface, said bioscaffold being produced by harvesting the soft tissue, hard tissue and soft-hard tissue interface from a mammalian cadaver, subjecting said interface only to targeted ultrasonication, and contacting said soft tissue, hard tissue, and interface with detergents and chemical oxidants to remove extracellular matrix materials, wherein the targeted ultrasonication of said interface results in removal of at least 90% of cells from said interface while retaining the tissues' and tissue interface's native biomechanical integrity, thereby rendering the bioscaffold host-compatible and suitable for surgical tissue interface reconstruction.

7. The bioscaffold according to claim 6, wherein said bioscaffold comprises a tendon, bone, and tendon-bone interface.

8. The bioscaffold according to claim 6, wherein said bioscaffold comprises a ligament, bone, and ligament-bone interface.

9. The bioscaffold according to claim 6, wherein said composite tissue was obtained from an allogeneic source.

10. The bioscaffold according to claim 6, wherein said composite tissue was obtained from a xenogeneic source.

11. The bioscaffold according to claim 6, wherein said bioscaffold is sterile.

12. The bioscaffold according to claim 6, wherein said bioscaffold is freeze-dried.

13. The bioscaffold according to claim 6, wherein said bioscaffold is aseptically packaged in a sterile container.

14. The bioscaffold according to claim 6, further being contacted with cells harvested from the graft recipient for reseeding of the bioscaffold prior to implantation into the graft recipient.

15. The bioscaffold according to claim 6, wherein said bioscaffold is used for reconstruction of an upper extremity, a lower extremity, a joint, pelvic floor, or for muscle reinforcement.

* * * * *